(12) United States Patent
Geyer et al.

(10) Patent No.: US 9,603,724 B2
(45) Date of Patent: Mar. 28, 2017

(54) ROBUST SWING LEG CONTROLLER UNDER LARGE DISTURBANCES

(71) Applicant: CARNEGIE MELLON UNIVERSITY, a Pennsylvania Non-Profit Corporation, Pittsburgh, PA (US)

(72) Inventors: Hartmut Geyer, Pittsburgh, PA (US); Ruta P. Desai, Pittsburgh, PA (US)

(73) Assignee: Carnegie Mellon University, a Pennsylvania Non-Profit Corporation, Pittsburgh, PA (US)

( * ) Notice: Subject to any disclaimer, the term of this patent is extended or adjusted under 35 U.S.C. 154(b) by 68 days.

(21) Appl. No.: 14/470,277

(22) Filed: Aug. 27, 2014

(65) Prior Publication Data
US 2015/0066156 A1    Mar. 5, 2015

Related U.S. Application Data

(60) Provisional application No. 61/959,564, filed on Aug. 27, 2013, provisional application No. 61/959,561, filed on Aug. 27, 2013.

(51) Int. Cl.
| | |
|---|---|
| *A61F 2/64* | (2006.01) |
| *A61F 2/70* | (2006.01) |
| *A61F 2/60* | (2006.01) |
| *A61F 2/68* | (2006.01) |
| *A61F 2/76* | (2006.01) |

(52) U.S. Cl.
CPC .............. *A61F 2/605* (2013.01); *A61F 2/64* (2013.01); *A61F 2/68* (2013.01); *A61F 2002/6827* (2013.01); *A61F 2002/701* (2013.01); *A61F 2002/704* (2013.01); *A61F 2002/762* (2013.01);
(Continued)

(58) Field of Classification Search
None
See application file for complete search history.

(56) References Cited

U.S. PATENT DOCUMENTS

| | | |
|---|---|---|
| 6,755,870 B1 | 6/2004 | Biedermann et al. |
| 7,295,892 B2 | 11/2007 | Herr et al. |

(Continued)

FOREIGN PATENT DOCUMENTS

| | | |
|---|---|---|
| EP | 1871308 B1 | 8/2010 |
| WO | 2010088635 A1 | 8/2010 |

(Continued)

*Primary Examiner* — David H Willse
(74) *Attorney, Agent, or Firm* — David G. Oberdick; Michael G. Monyok

(57) ABSTRACT

Local swing leg control was developed that takes advantage of segment interactions to achieve robust leg placement under large disturbances while generating trajectories and joint torque patterns similar to those observed in human walking and running. The results suggest the identified control as a powerful alternative to existing swing leg controls in humanoid and rehabilitation robotics. Alternatively, a detailed neuromuscular model of the human swing leg was developed to embody the control with local muscle reflexes. The resulting reflex control robustly places the swing leg into a wide range of landing points observed in human walking and running, and it generates similar patterns of joint torques and muscle activations. The results suggest an alternative to existing swing leg controls in humanoid and rehabilitation robotics which does not require central processing.

25 Claims, 25 Drawing Sheets

(52) U.S. Cl.
CPC .......... *A61F 2002/7625* (2013.01); *A61F 2002/7645* (2013.01)

(56) References Cited

U.S. PATENT DOCUMENTS

| | | |
|---|---|---|
| 8,366,788 B2 | 2/2013 | Moser et al. |
| 2010/0324699 A1 | 12/2010 | Herr et al. |

FOREIGN PATENT DOCUMENTS

| | | |
|---|---|---|
| WO | 2011096965 A2 | 8/2011 |
| WO | 2012094486 A1 | 7/2012 |
| WO | 2013123291 A1 | 8/2013 |
| WO | 2014043681 A2 | 3/2014 |

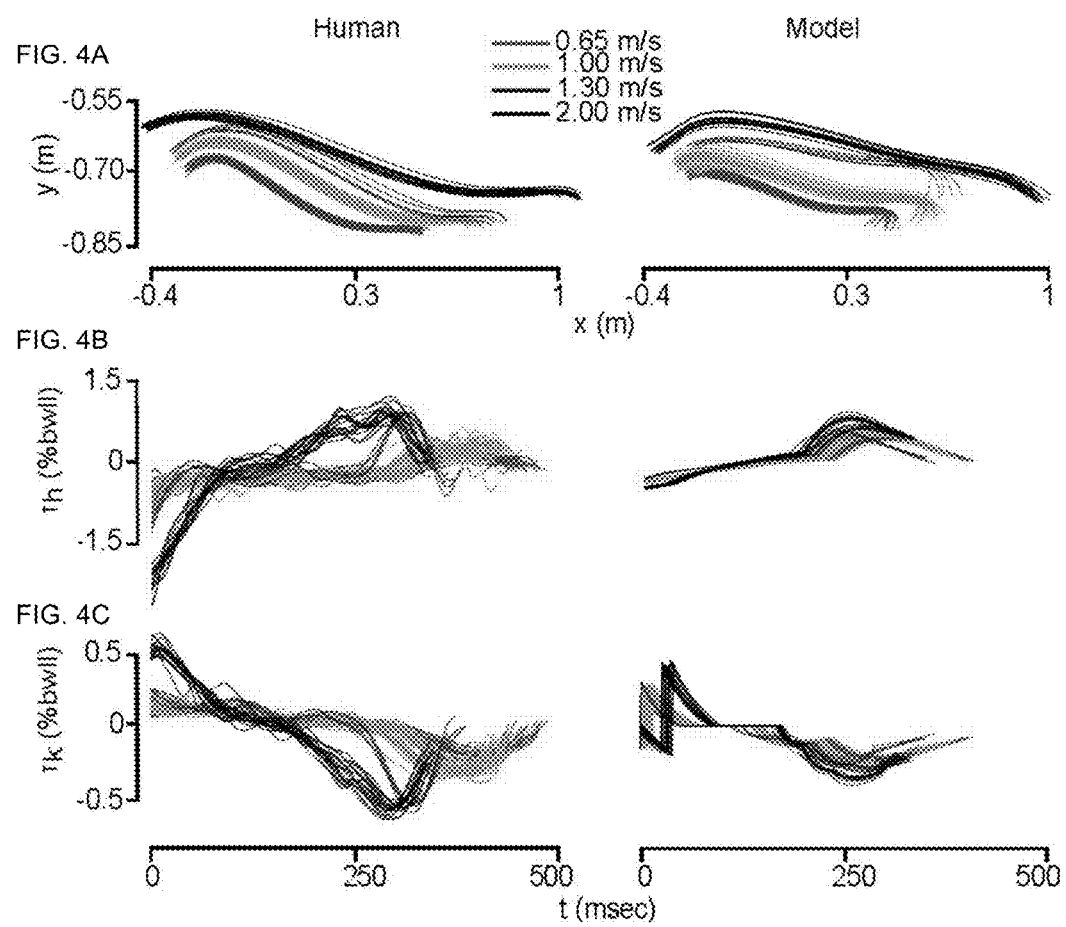
FIGS. 4A-C

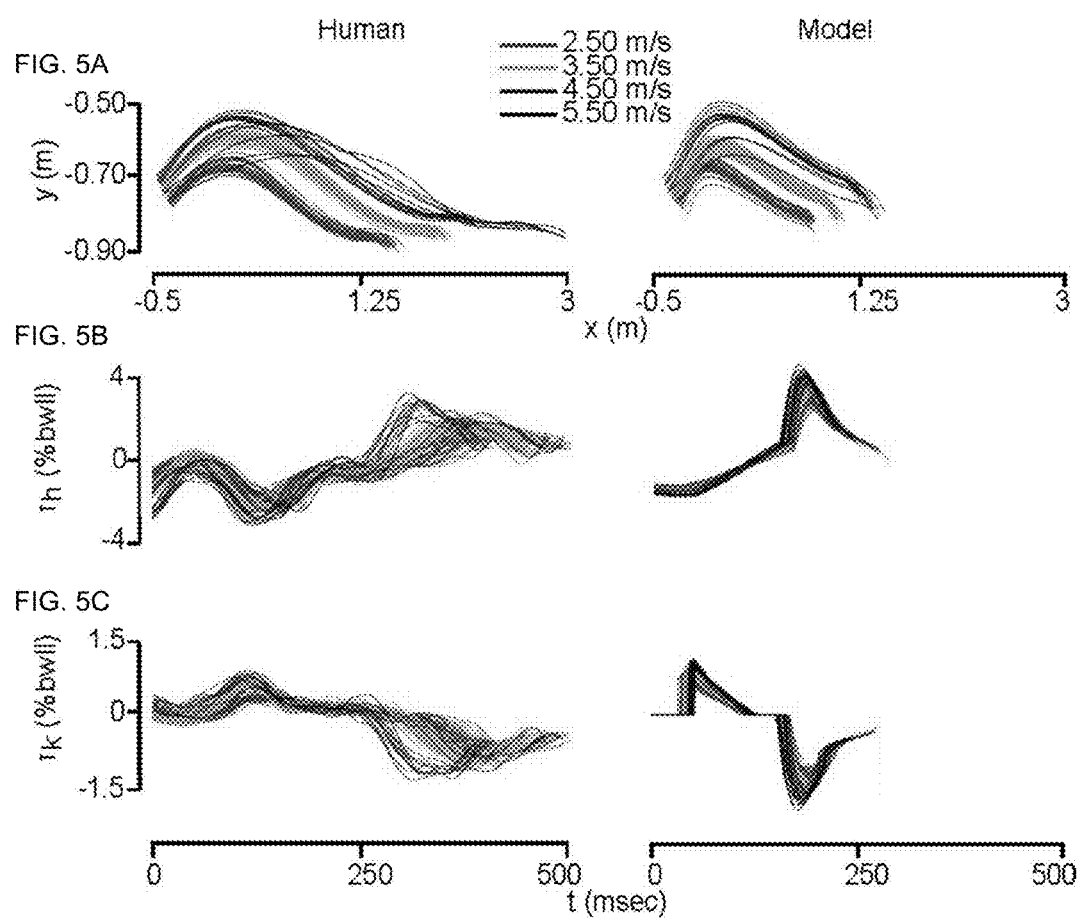
FIGS. 5A-C

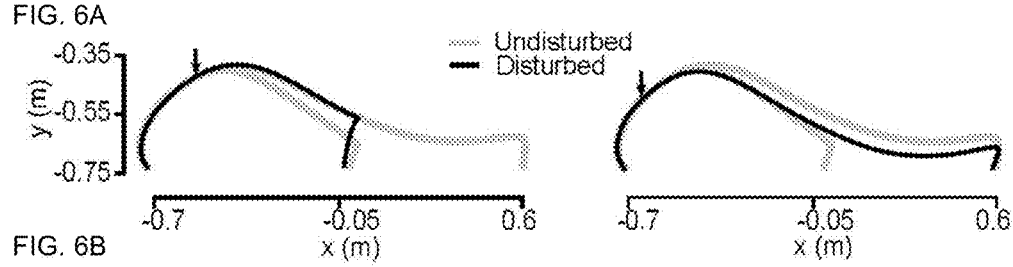
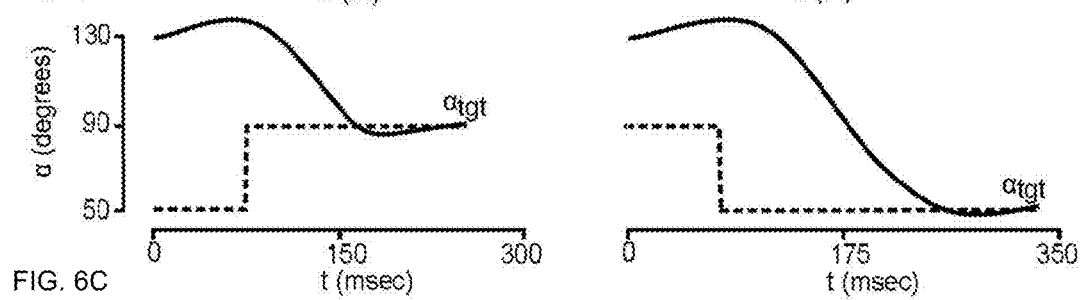
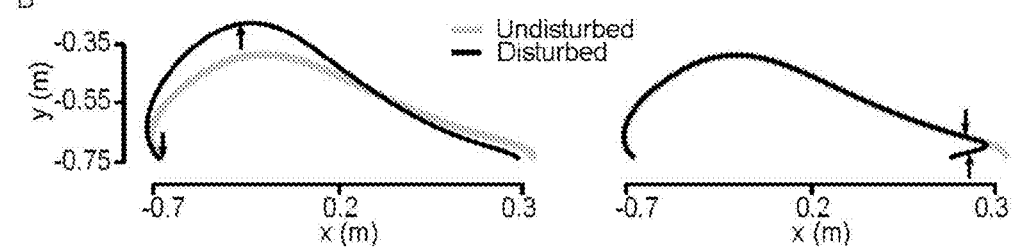
FIGS. 6A-C

FIGS. 12A-B(iii)

ROBUST SWING LEG CONTROLLER UNDER LARGE DISTURBANCES

CROSS-REFERENCE TO RELATED APPLICATIONS

This application claims priority to U.S. Provisional Application Ser. No. 61/959,564, titled ROBUST SWING LEG CONTROLLER UNDER LARGE DISTURBANCES, filed Aug. 27, 2013, and to U.S. Provisional Application Ser. No. 61/959,561, titled MUSCLE-REFLEX CONTROL OF ROBUST SWING LEG PLACEMENT, filed Aug. 27, 2013, both incorporated by reference herein in its entirety.

STATEMENT REGARDING FEDERALLY-SPONSORED RESEARCH AND DEVELOPMENT

This invention was made with government support under the National Science Foundation EEC 0540865 and National Institute of Health 1R01HD075492-01. The government has certain rights in this invention.

BACKGROUND

Swing leg placement is vital to stability in legged robots and animals. Without placing the feet into proper target points on the ground, legged systems fail to balance dynamically. These targets have been identified with simplified point-mass models including the linear inverted pendulum for standing and walking, and the spring-mass system for running. The models predict foot placement targets which stabilize gait in response to a disturbance such as an external push or an unexpected change in the ground level. However, they do not reveal how the segmented legs of humans and humanoids can actually reach these targets.

The most common approach to generating swing leg motions in humanoids uses trajectory planning and tracking. In this approach, trajectories for all leg joints are planned either based on optimization over deviations from the foot placement targets or by spline interpolation between consecutive placement targets. Once generated, these reference trajectories are tracked via proportional-derivative control at the joint levels. Planning and tracking of swing-leg trajectories requires central control over all leg joints, which limits the application of this approach to powered prosthetic limbs which replace only part of the human body.

Although alternative approaches have been explored in rehabilitation robotics, tracking predefined joint patterns remains the state of the art in the control of powered artificial legs. For instance, current leg prostheses mimic human joint impedances that have been recorded in experiments. Bound to these predefined patterns, handling gait disturbances still requires event detection, automatic classification, and the implementation of deliberate joint trajectories to counter these disturbances, hampering practical implementations of autonomous powered legs that achieve robust swing placement under large disturbances.

Animal and human legs by contrast demonstrate robust swing placement with remarkable autonomy. From early work on mesencephalic cats to recent investigations on paralyzed cats and rats with drug administration and epidural stimulation, experiments have shown that animals can seamlessly adapt their leg behavior throughout stance and swing, to different speeds and gaits without central planning by the brain. These observations suggest that a substantial part of leg control in animal and human locomotion is generated by spinal circuits which adapt to changes in the environment.

BRIEF SUMMARY OF THE INVENTION

A control for swing leg motions is described herein, inspired by observations on local control in animal and human locomotion. It is based on local feedbacks and does not require predefined swing leg trajectories to robustly place the leg into target points on the ground. In one embodiment, a control was developed guided by the segment dynamics of a double pendulum. The control is structured around a sequence of three tasks that include flexing the leg into a clearance length, advancing the leg into a target angle, and extending it until ground contact. Although this sequence can be enforced with strict trajectory tracking, energy efficient and modular artificial legs in rehabilitation robotics was targeted and hence the developed control takes advantage of passive swing leg dynamics and decouples individual hip and knee controls wherein the motion of the hip and the knee joints are determined without enforcing reference trajectories of either the hip or the knee joint. Thus, the developed control does not require tracking reference trajectories of either the hip or the knee joint. The performance of the control in simulations was tested with a more anthropomorphic swing leg that considers human-like segment mass and inertia distribution as well as the effect of translational hip acceleration. It was demonstrated that the identified control can achieve swing leg placement into a large range of target points, and that this placement is robust to disturbances in initial conditions and to sudden changes in the target during swing, and that the resulting swing leg trajectories and joint torque patterns compare to those of human walking and running.

An alternative embodiment of a control for swing leg motions was developed based on local feedbacks and does not require predefined swing leg trajectories to robustly place the leg into target points on the ground. To compare the identified control with human swing leg behavior at the level of muscle activations and to prepare a transfer to powered prosthetic legs that react like human limbs, a neuromuscular control model of the human leg in swing was developed that embodies the identified control with local reflexes. The resulting reflex control robustly places the swing leg into target angles from 50 deg to 75 deg which cover observed landing leg angles for a wide range of human walking and running speeds. In addition, the control generates swing patterns that share the main features of human swing leg patterns for the ankle trajectory, joint torques, and muscle activations. The example embodiments described herein suggest an alternative to existing swing leg controls including, but not limited to, humanoid and rehabilitation robotics which does not require central processing.

BRIEF DESCRIPTION OF THE DRAWINGS

FIGS. 4A-C illustrates the observed and predicted swing leg patterns in walking, respectively. The ankle trajectories (A), hip and knee torques (B&C) during multiple swing phases (individual traces) are compared between human walking and model prediction at four different walking speeds (color coded). For the model, the initial joint positions and speeds as well as the hip translational accelerations are taken from the corresponding human swing motions. The coordinates of the foot point in A are given with respect to a world frame that originates at the initial position of the hip. The torques in B and C are normalized to percent of body weight times leg length (% bwll);

FIGS. 5A-C illustrates the observed and predicted swing leg patterns in running, respectively. See caption of FIG. 4 for explanations. Note that for only one swing at 3.5 ms$^{-1}$, the model engaged knee stop (knee torque spike at end.);

FIGS. 6A-C illustrates the Reaction to disturbances during swing. The reaction to disturbances during swing is shown for large changes in the target leg angle $\alpha$ and during simulated obstacle encounters for characteristic swing phases with initial conditions that match human walking at 1.3 ms$^{-1}$. Undisturbed swing phases are shown in gray and disturbed ones in black. (A) The target angle (dashed line) is changed at 75 ms into the swing from 50 deg to 90 deg (left column) and vice versa (right column). The arrows mark the foot point position at the time of change. (B) An external impulse of 15 Ns is applied to the foot point in early (left) and late swing (right), resulting in an elevated foot point trajectory and premature landing, respectively. The arrows indicate the start and end of the force application;

DETAILED DESCRIPTION OF THE INVENTION

Swing Leg Model

Figure 1A:
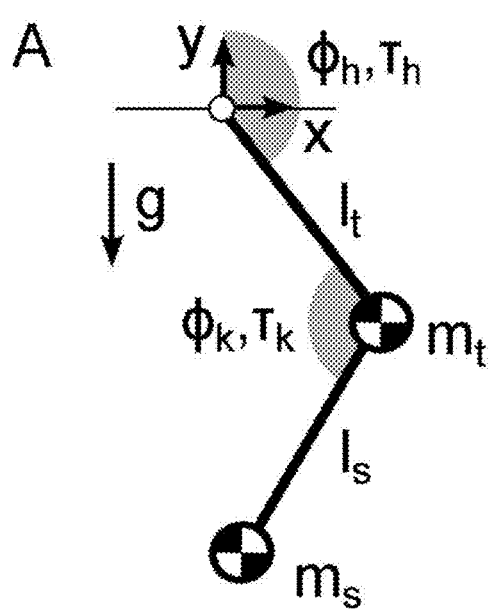
FIGS. 1A and 1B illustrate swing leg models: (A) Conceptual double pendulum model with point masses at the segment ends; and (B) More realistic swing leg model with human-like segment mass distribution and hip translational accelerations as external input.

In human and humanoids, leg placement is largely achieved by the motion of the hip and knee while the ankle contribution can be neglected. To develop intuition about the control strategies for swing leg placement, the classic double pendulum with the thigh and shank represented as massless rods of lengths $l_t$ and $l_s$ with point masses $m_t$ and $m_s$ attached to their ends was used in one embodiment (FIG. 1A). The hip is connected to an immovable trunk at the origin of the world frame, and the joint angles $\phi_h$ and $\phi_k$ are measured as shown in FIG. 1A. The resulting equations of motion are:

$$((m_t+m_s)l_t-m_s l_s \cos\phi_k)l_t \ddot{\phi}_h = \tau_h+\tau_k-m_s l_t l_s \cos\phi_k \ddot{\phi}_k + m_s l_s l_t \sin\phi_k(\dot{\phi}_k-\dot{\phi}_h)^2+(m_t+m_s)l_t g \sin\phi_h \quad (1)$$

$$m_s l_s^2 \ddot{\phi}_k = \tau_k + m_s l_s(l_s - l_t \cos\phi_k)\ddot{\phi}_h + m_s l_s l_t \sin\phi_k \dot{\phi}_h^2 - m_s l_s g \sin(\phi_k-\phi_h) \quad (2)$$

for the hip and knee, respectively, where $\tau_h$ and $\tau_k$ are the applied hip and knee torques.

Figure 1B:
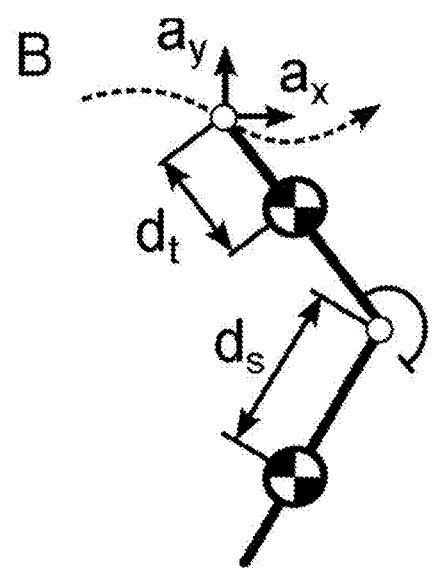

In addition to the conceptual model, the performance of the control with a more realistic simulation model of human swing motions was tested (FIG. 1B). In this second model, the segment inertial properties are based on anthropomorphic data obtained from scaling tables for a human with a body weight and height of 80 kg and 180 cm ($m_t$=7 kg, $m_s$=4.3 kg, $d_t$=21.7 cm, $d_s$=30.3 cm, $l_t$=43 cm, $l_s$=43 cm). Moreover, the model includes a knee stop realized by a restoring torque:

$$\tau_k^{res} = \begin{cases} k_\phi(\phi_k-\phi_{max})(1+\dot{\phi}_k/\dot{\phi}_{max}), & \dot{\phi}_k > -\dot{\phi}_{max} \\ & \phi_k > \phi_{max} \\ 0, & \text{otherwise} \end{cases} \quad (3)$$

($\phi_{max}$=175 deg, $\dot{\phi}_{max}$=0.01 rads$^{-1}$, $k_\phi$=17.2 Nmrad$^{-1}$) and accounts for hip translational accelerations ($\alpha_x$, $\alpha_y$) in later comparisons to human swing phases in steady walking and running.

Modular Local Control

Figure 2A:
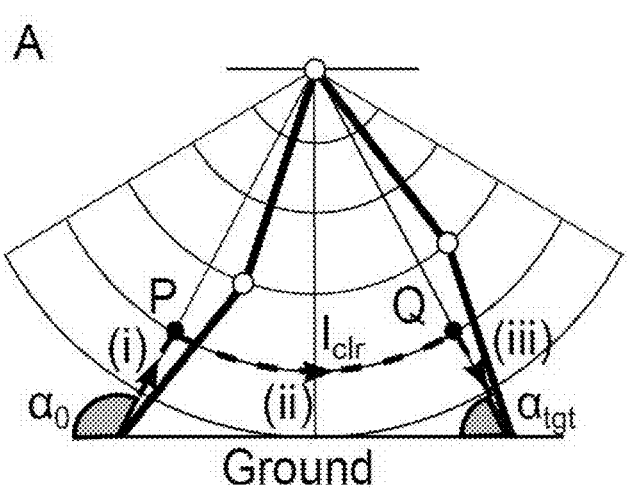
FIGS. 2A and 2B illustrate swing leg control. (A) Sequence of natural control tasks for reaching a target placement while guaranteeing foot ground clearance. (B) Functional relationship between $\alpha$ and $\phi_h$ and $\phi_k$. With $\gamma=90-\phi_k/2$ and $\beta=180-\gamma-\phi_h$, $\alpha$ relates to $\phi_h$ and $\phi_k$ as $$\alpha = \phi_h - \frac{\phi_k}{2};$$
Figure 2B:
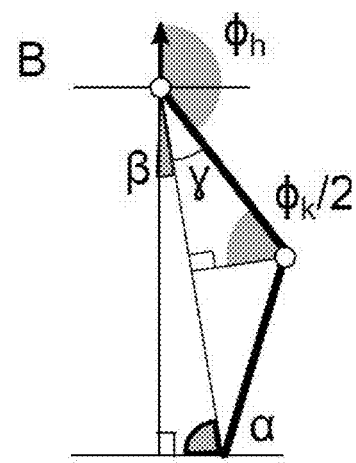
Figure 2C:
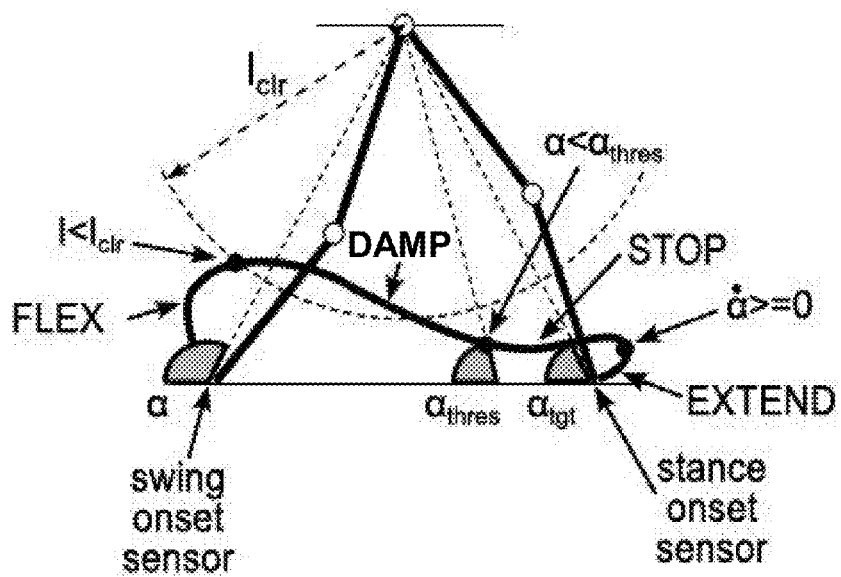
FIGS. 2C and 2D illustrate individually the knee control and the hip control in a typical swing phase.

In addition to the fundamental goal placing the foot into target points, the swing leg motion is subject to the constraint that the foot point needs to clear the ground or an obstacle. We represent both, the placement goal and the clearance constraint, by two control variables, the target leg angle $\alpha_{tgt}$ and the clearance leg length $l_{clr}$, respectively (FIGS. 2A and 2C). Assuming equal segment lengths $l_t=l_s$ (good approximation for human legs) in the remainder of this paper, the leg angle is given by $$\alpha = \phi_h - \frac{\phi_k}{2}$$

and the leg length resolves to $$l = 2l_t \sin\frac{\phi_k}{2}$$

(FIG. 2B).

FIG. 2A outlines a natural sequence of three control tasks which reflects the objective and constraint. First, starting at the ground level from an initial leg angle $\alpha_0$, the clearance constraint requires the leg to flex to at least the clearance length $l_{clr}$ (reached at P). Second, the control focus shifts to advancing the swing leg to the target angle $\alpha_{tgt}$ (reached at Q). And the final task is to extend the leg until ground contact.

Although this sequence of control tasks can be strictly enforced with classical state feedback control, tracking predefined trajectories is avoided for two reasons. Similar to humans, we seek to take advantage of the passive dynamics that the swing leg provides to lessen the required torques. In addition, we seek decoupled joint controls as much as possible to modularize the control. Both goals target autonomous and modular replacement legs in rehabilitation robotics. As a consequence, the swing leg control is structured around functionally distinct hip and knee joint controls.

Figure 2D:
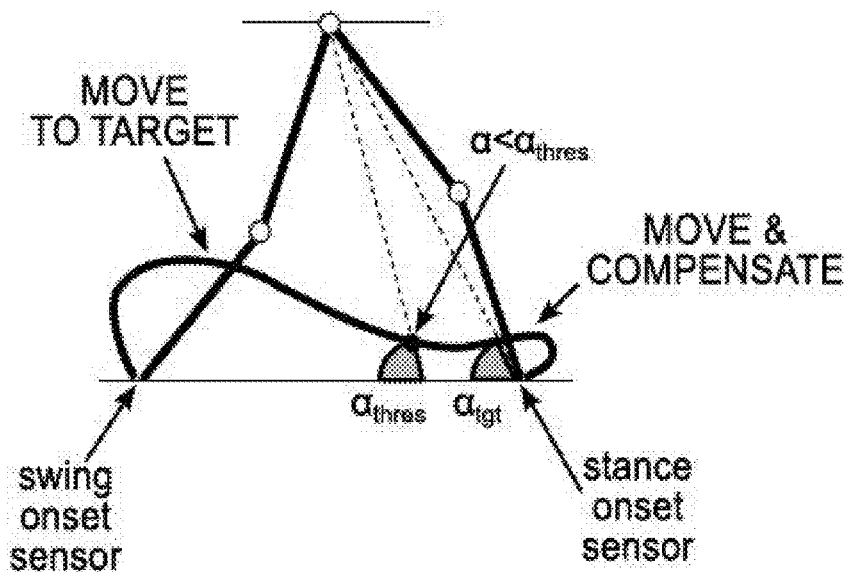

FIG. 2C outlines the various distinct phases of the knee control of the typical swing phase: flex, damp, stop, and extend. The Flex phase begins from the initial point of raising a foot in contact with the ground to the point where the current leg length is equal to or less than the clearance leg length $l_{clr}$, thereby beginning the Damp phase. The Damp phase dampens the motion of the leg along the leg lengthening axis modulated by how close the leg angle is to the target angle and by how fast the leg angle is moving towards the target angle according to equation 7, until the current leg angle is smaller than the threshold angle, which initiates the Stop phase. The Stop phase reduces and reverses the leg angular speed in preparation of the Extend phase that will lower the foot on to the target position causing the foot to move backwards when the leg is extended. FIG. 2D further illustrates the various phases of the hip control of the typical swing phase: move to target and move & compensate. The Move to target phase begins from the initial point of raising a foot in contact with the ground. In this phase the hip control seeks to place the leg into the target angle. When the leg angle reaches the threshold leg angle, the hip control switches to the Move & Compensate phase in which the torque generated by the hip control is augmented with a compensation torque that compensates for the effect of torque produced around the knee on the hip.

A. Hip Control

The hip control is active throughout the swing and its primary function is to move the leg into the target angle $\alpha_{tgt}$. The specific control input $\tau_h^\alpha$ is given by $$\tau_h^\alpha = k_p^\alpha(\alpha_{tgt}-\alpha)-k_d^\alpha \dot{\alpha} \quad (4)$$

where $k_p^\alpha$ and $k_d^\alpha$ are proportional and derivative gains, respectively. Note that a negative input tends to flex the hip. In addition to the angle control, the hip control receives a second input $\tau_h^{iii}$ from the knee control, $$\tau_h = \tau_h^\alpha + \tau_h^{iii}, \quad (5)$$

during the last, leg extension stage in the control sequence (after reaching Q). The purpose of $\tau_h^{iii}$ is detailed in the next section on knee control. It is the only crossover input between the joints.

B. Knee Control

The knee control's primary function is to regulate leg length. However, due to the influence of the knee angle on both, leg length and leg angle, the control is more involved. It is separated into the three natural control tasks outlined before (FIG. 2A).

To accomplish the first control task of reaching a minimum clearance $l_{clr}$ in the initial swing, we take advantage of the passive swing leg dynamics. Equation 2 shows that while the Coriolis, centrifugal and gravitational terms always tend to extend the knee, a negative hip acceleration tends to flex the knee. The hip control (Eq. 4) generates negative hip acceleration initially to drive the leg into the target angle. The resulting passive, negative knee acceleration sufficiently overcomes the opposing Coriolis, centrifugal and gravitational accelerations as long as the leg angle $\alpha$ increases, $\dot{\alpha}>0$ or equivalently $\dot{\phi}_k<2\dot{\phi}_h$ (backward motion of foot point). In that case, no input $\tau_k$ is required to flex the leg, as the increase in $\alpha$ reinforces hip flexion control and, in turn, passive knee flexion. If on the other hand $\dot{\alpha}\leq0$, the passive knee flexion is no longer sufficient and the leg tends to scuff the foot. Thus we implement active knee flexion control only in proportion to how fast the leg moves forward, $$\tau_k^i = \begin{cases} k^i \dot{\alpha}, & \dot{\alpha} \leq 0 \\ 0, & \dot{\alpha} > 0 \end{cases}, \quad (6)$$

where $k^i$ is a proportional gain.

Once the leg length as shortened past the clearance length, $l < l_{clr}$, the knee control switches to the second task of damping the knee so that the leg angle control by the hip can take full effect (Eq. 4). We realize this task with a damping input $$\tau_k^{ii} = \begin{cases} -k^{ii} \dot{\phi}_k, & \dot{\phi}_k \leq 0 \\ -k^{ii} \dot{\phi}_k (\alpha - \alpha_{tgt})(\dot{\phi}_k + \dot{\alpha}), & \dot{\phi}_k > 0 \,\&\, \dot{\phi}_k > -\dot{\alpha} \\ 0, & \text{otherwise} \end{cases} \quad (7)$$

that is pure when the knee flexes ($\dot{\phi}_k \leq 0$) and modulated when it extends ($\dot{\phi}_k > 0$), with a proportional gain of $k^{ii}$. The implementation avoids the large torques that a precise tracking of $l = l_{clr}$ would incur fighting the passive swing leg dynamics (FIG. 2A). In particular, when the hip control stops pulling forward, all interaction terms in equation 2 create passive knee extension. The first modulation term ($\alpha - \alpha_{tgt}$), enables this passive extension when $\alpha$ approaches its target, easing the third control task. However, when the leg swings faster at higher speeds, passive knee extension amplifies markedly due mainly to the Coriolis acceleration $l_t \sin \phi_k \dot{\phi}_h^2$, and the second modulation term ($\dot{\phi}_k + \dot{\alpha}$), prevents a premature landing of the leg. This term compares the knee extension velocity to the approach velocity $\dot{\alpha}$ (negative when moving forward). If the knee extends faster than the leg moves towards its target angle, damping torque is proportionally activated; otherwise, no control torque is applied.

The final knee control task of stopping swing and extending the leg into the target is initiated when the leg angle passes a threshold $\alpha_{thr} = \alpha_{tgt} + \Delta\alpha_{thr}$ and is realized with two functional components. The first component generates a stopping knee-flexion torque $$\tau_k^{iii} = \begin{cases} -k^{stp}(\alpha_{thr} - \alpha)\left(1 - \dfrac{\dot{\alpha}}{\dot{\alpha}_{max}}\right), & \alpha < \alpha_{thr} \\ & \dot{\alpha} < \dot{\alpha}_{max} \\ 0, & \text{otherwise} \end{cases} \quad (8)$$

that is inspired by nonlinear contact models, where $k^{stp}$ is a proportional gain, $\alpha_{thr} - \alpha$ corresponds to 'ground indentation' and $\dot{\alpha}_{max}$ is the return velocity at which 'ground resistance' vanishes. The stopping torque works well only if its coupling into the hip motion is canceled and we apply the compensation torque $$\tau_h^{iii} = -2\tau_s^{iii} \quad (9)$$

at the hip. To motivate this particular compensation, consider equations 1 and 2 at hip and knee angles of 180 deg (vertical leg position). The equations then simplify to $$(m_t + 2m_s)l_t^2 \ddot{\phi}_h = \tau_h + \tau_k + m_s l_t^2 \ddot{\phi}_k \quad (10)$$

$$m_s l_t^2 \ddot{\phi}_k = \tau_k + 2 m_s l_t^2 \ddot{\phi}_h \quad (11)$$

where we used the assumption $l_s = l_t$. Using equation 11 to substitute $\ddot{\phi}_k$ in equation 10, we get $$m_s l_t^2 \ddot{\phi}_h = \tau_h + 2\tau_k$$

for the hip equation, which shows that a compensation torque $\tau_h = -2\tau_k$ cancels the effect of knee torque on the hip motion.

The second functional component engages when the leg has slowed down to zero angular speed $\dot{\alpha} = 0$, upon which a deliberate extension component is added to the knee torque, $$\tau_k^{iii'} = \tau_k^{iii} + k_{ext}(l_0 - l) \quad (12)$$

where $k^{ext}$ is a proportional gain and $l_0 = l_t + l_s$. This active knee extension ensures that the leg reaches down to the ground.

Results and Discussion

The control developed in the previous section is based on the simple double pendulum as a conceptual model (FIG. 1A). However, to test the control performance, a swing leg model was used that considers human-like segment mass distribution and the effect of hip translational accelerations generated by the body (FIG. 1B). With this more realistic model, the control parameters were tuned to achieve robust leg placement into a realistic range of target angles assuming large variations in initial conditions. The predicted patterns of the foot point motion and the joint torques were then compared with those of human walking and running, and evaluated the quality of the leg placement generated by the local feedback control during sudden changes in swing leg targets as well as during horizontal pushes on the foot point that simulate obstacle encounters.

A. Leg Placement into Arbitrary Targets

The initial leg configuration is set to $\phi_{h,0} = 220$ deg and $\phi_{k,0} = 175$ deg ($\alpha_0 = 132.5$ deg), the clearance leg length is fixed at $l_{clr} = 5$ cm, and the control gains of the local feedback control are hand-tuned with the goal of minimizing the error between the target leg angle and the actual landing angle for a large range of initial joint velocities and target angles. Simultaneously, peak joint torques are tuned to be within the peak torques observed in human walking and running. Note that the hip is still assumed to be hinged during tuning as it is unclear what external translational accelerations should be applied in this process. The resulting set of control parameters is shown in Table 1.

TABLE 1

Control parameters values. Values in parentheses are gains adapted for walking & running respectively.

| parameter | value | parameter | value |
|---|---|---|---|
| $k_p^\alpha$ | 110 (50/150) Nmsrad$^{-1}$ | $k^i$ | 13 Nmsrad$^{-1}$ |
| $k_d^\alpha$ | 8.5 (5.5/8.5) Nmsrad$^{-1}$ | $k^{ii}$ | 5.5 Nmsrad$^{-1}$ |
| $k^{stp}$ | 250 (60/160) Nmsrad$^{-1}$ | $\dot{\alpha}_{max}$ | 10 rads$^{-1}$ |
| $k^{ext}$ | 200 N | $\alpha_{thr}$ | $\alpha_{tgt} + 8$ deg |

FIG. 3 shows the resulting control performance for target angles $\alpha_{tgt} = 50 \ldots 130$ deg that include typical human landing leg angles and for initial joint velocities $\dot{\phi}_{h,0} = -5 \ldots 5$ rads$^{-1}$ and $\dot{\phi}_{k,0} = 10 \ldots 0$ rads$^{-1}$ that cover the experimental data on initial joint velocities in human locomotion ($\dot{\phi}_{h,0} = -4 \ldots 2$ rads$^{-1}$ and $(i)_{k,0} = 7 \ldots -1$ rads$^{-1}$). The identified feedback control can achieve low target placement errors with an average error of 1.4 deg and a maximum error of 5.2 deg throughout the large ranges of target angles and initial joint velocities. Similar results hold for different ground clearance constraints and initial leg configurations ($l_{clr} = 5.8 \ldots$ cm and $\alpha_0 = 132, 140 \ldots$ deg).

B. Comparison to Human Walking and Running

For the comparison to human swing motions, multiple swing leg trajectories of a subject walking from 0.65 ms$^{-1}$ and 2 ms$^{-1}$ and running from 2.5 ms$^{-1}$ to 5.5 ms$^{-1}$ were recorded, covering slow to fast walking as well as slow to fast running. The left columns in FIGS. 4A-C and 5A-C show the ankle trajectories (A) and the corresponding hip and knee torques (B and C, obtained from inverse dynamics) observed during human swing in walking and running at the different speeds.

The model-predicted swing leg patterns are similar to the observed ones in walking. The right column in FIGS. 4A-C shows the model-predicted swing phase motion of the foot point (tip of shank segment) and the corresponding joint torque patterns. (For all speeds, the model's target angle is $\alpha_{tgt}$=70 deg, which equals the observed landing angle $\alpha_f$=70±3 deg.) Also, hip translational accelerations are applied in the model based on the observed hip accelerations for each swing phase. As a result, the hip control gains had to be adjusted to one set of lower values for all walking trials and of higher values for all running trials, Tab. 1) The foot point motion has a similar range and shape for all four walking speeds (A), and the hip and knee torques have similar magnitudes and gross behavior (B and C). In the model, the hip torque pattern is generated by the target angle control (Eq. 4) throughout swing, except for the sharp rise in hip extension torque which appears in the second half of swing due to the knee compensation $\tau_h^{iii}=-2\tau_k^{iii}$ (Eqs. 5 and 9). This sharp rise also occurs in the knee torque pattern and is generated by the knee stopping torque (Eq. 8). One marked difference in the knee torque pattern appears at 2.00 ms$^{-1}$ walking, where, before the knee damping occurs that prevents leg flexion past the clearance length (Eq. 7), the model shows an initial knee flexion torque to actively prevent scuffing the foot (Eq. 6). This initial flexion torque is not visible in human walking. The difference is related to the much larger initial hip flexion torque that humans use at this speed, which passively flexes the knee and thus prevents foot scuffing. It points to a speed-dependent increase in the hip control gains not included in the model.

In contrast to walking, the predicted patterns for running have a shorter stride length and a clearly faster swing time than present in human running (FIGS. 5A-C). Despite these differences, the shapes of the torque patterns match human data in general (B and C). The shape of the hip torque pattern is similar between walking and running in the model. Except for an initial modulation, this general shape is also preserved in the human hip torque pattern between walking and running. By contrast, the knee torque pattern shows an added, initial period of silence in running which is present in both the model and the human data. This silent period occurs in the model as the initial knee angle in the swing phase of running ($\phi_{k,0}$=149±2.5 deg) is more extended than in walking ($\phi_{k,0}$=120±2 deg), and the knee passively flexes before the leg reaches the clearance length where the damping torque engages (Eq. 7).

The short swing phase in running is caused mainly by an increased proportional gain $k_p^\alpha$ for the leg angle control at the hip (Eq. 4 and Table 1). This modification in the model was required, because otherwise the passive leg flexion by the hip control is too weak and the large hip translational accelerations in running force the leg into an early landing. The modification also entails a larger gain $k^{stp}$ for the stopping control (Eq. 8 and Table 1).

C. Reactions to Target Changes and Obstacle Encounters

In addition to comparing the predicted swing leg patterns to human swing motions, the performance of the control in the presence of disturbances was tested. First, sudden changes in the target angle were considered. FIG. 6A shows the characteristic response of the model to changes in the target angle from $\alpha_{tgt}$=50 deg to $\alpha_{tgt}$=90 deg and vice versa (left and right columns, respectively), which are initiated at 75 ms into the swing phase. In both cases, the control rapidly adapts and guides the foot point into the new target position with negligible error. A similar performance for the same changes initiated later in the swing was observed (not shown), up to 150 ms from 50 deg to 90 deg (at which the leg angle crosses_$\alpha$=90 deg in the undisturbed swing) and up to 225 ms for the reverse change (which equals about 80% of the swing time of its corresponding undisturbed case).

FIG. 6B shows the characteristic response of the model to an impulse disturbance of 15 Ns in early and late swing (left and right columns). The impulse simulates obstacle encounters and is applied as a constant force applied to the foot point in the negative x-direction. The model shows an elevating response for the early disturbance and a premature landing for the late disturbance. Both responses are observed in human locomotion and often assumed to reflect two explicit control strategies. By contrast, the model shows these two behaviors as inherent outcomes of its placement control.

Figures 3A, 3B:
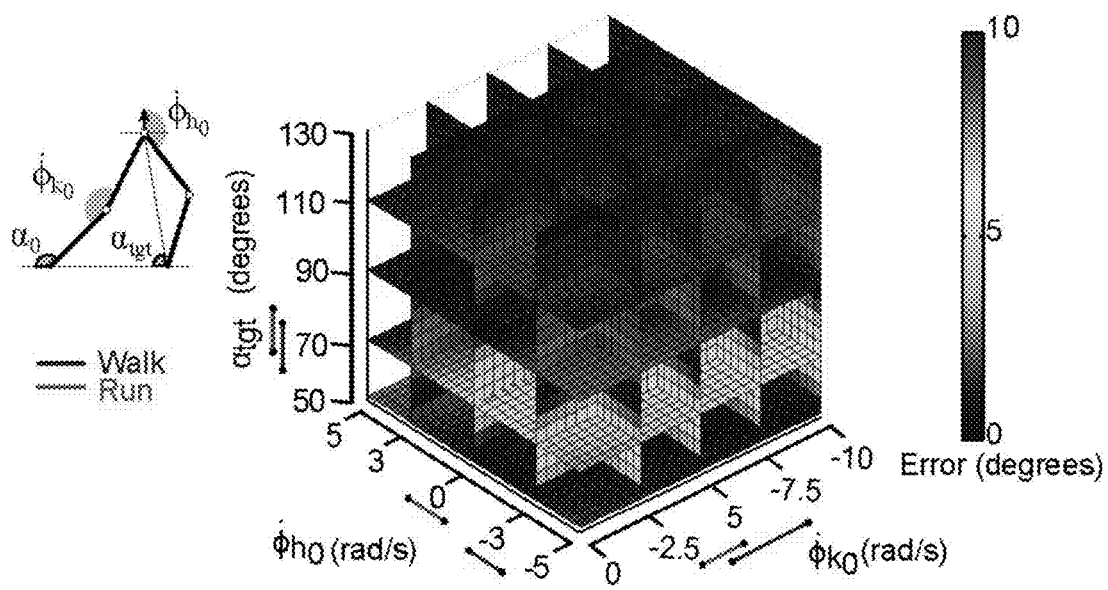
FIG. 3A is a representation of a simulation model of the present invention.
FIG. 3B is a plot of swing leg placement into arbitrary targets under large variation in initial conditions. The error $\Delta\alpha=\alpha_{tgt}-\alpha_l$ between the target angle and the achieved landing angle is shown as a color code for a large range of initial hip and knee velocities that cover the initial joint velocities observed in human locomotion from 0.65 ms$^{-1}$ to 5.5 ms$^{-1}$.

The results of the exemplary embodiments suggest that the control can achieve swing leg placement into a large range of targets for a wide range of walking and running speeds with robustness to disturbances in initial conditions and to sudden changes in the placement target during swing. In the simulation model, the control achieves leg placement into target angles ranging from 50 deg to 130 deg with an average error of 1.4 deg and a maximum error of 5.2 deg throughout a large range of initial joint velocities (FIG. 3B). This accuracy is maintained even when the target angles are suddenly changed during swing (FIG. 6A). This performance, generated by the developed control without the need to track reference trajectories of either the hip or the knee joint, is in stark contrast to current control approaches using trajectory tracking, which need to retune trajectories for different locomotion speeds and to provide explicit compensation trajectories when encountering disturbances.

In addition, the control generates swing patterns that share the main features of human swing leg patterns. In undisturbed swings, the control generates foot point and joint torque patterns that are similar to those patterns observed in human walking and running (FIGS. 4A-C and 5A-C). One major difference is the substantially shorter swing time in running in the model, which coincides with clearly shorter stride lengths. During simulated obstacle encounters in early and late swing, the model generates an elevating response and a premature landing, respectively (FIG. 6B). Both responses are well known behaviors in disturbed human swing phases. In contrast to generating these responses with explicitly triggered control, they are inherent to the identified leg placement control.

Figure 7:
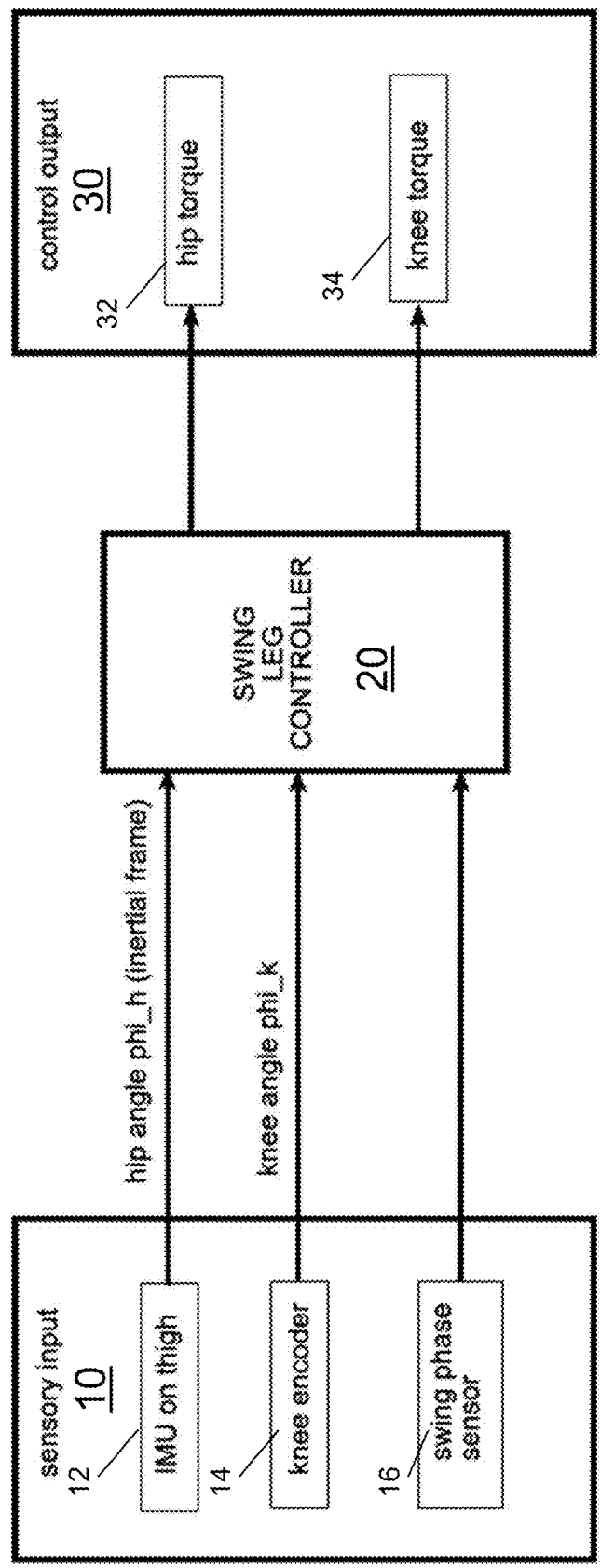
FIG. 7 is an overview of the system of the present invention.

Now turning to FIG. 7 that illustrates an overview of the system of the present invention. The present invention system includes sensory input 10, swing leg controller 20, and control output 30, each in communication with its adjacent sub-system module. Sensory input 10 collects data from an Inertial measurement unit (IMU) 12 to determine the current hip angle $\Phi_H$ and knee encoder 14 to determine current knee angle $\Phi_K$, and swing phase sensor 16 having contact sensors (not shown) to determine contact of the foot with the ground identifying the beginning and end of the swing phase. Sensory input 10 provides input to swing leg controller 20 for the calculation of key parameters discussed above to determine the positive or negative hip torque 32 and knee torque 34 to apply to the hip joint and/or the knee joint to satisfy a condition. The application of hip torque and knee torque is administered by Control Output 30. The Inertial measurement unit 12 is an electronic device that measures and reports on an object's velocity, orientation, and gravitational forces, using a combination of accelerometers and gyroscopes, sometimes also magnetometers. The knee encoder 14 is an electro-mechanical device that converts the angular position or motion of a shaft or axle to an analog or digital code.

Figure 8:
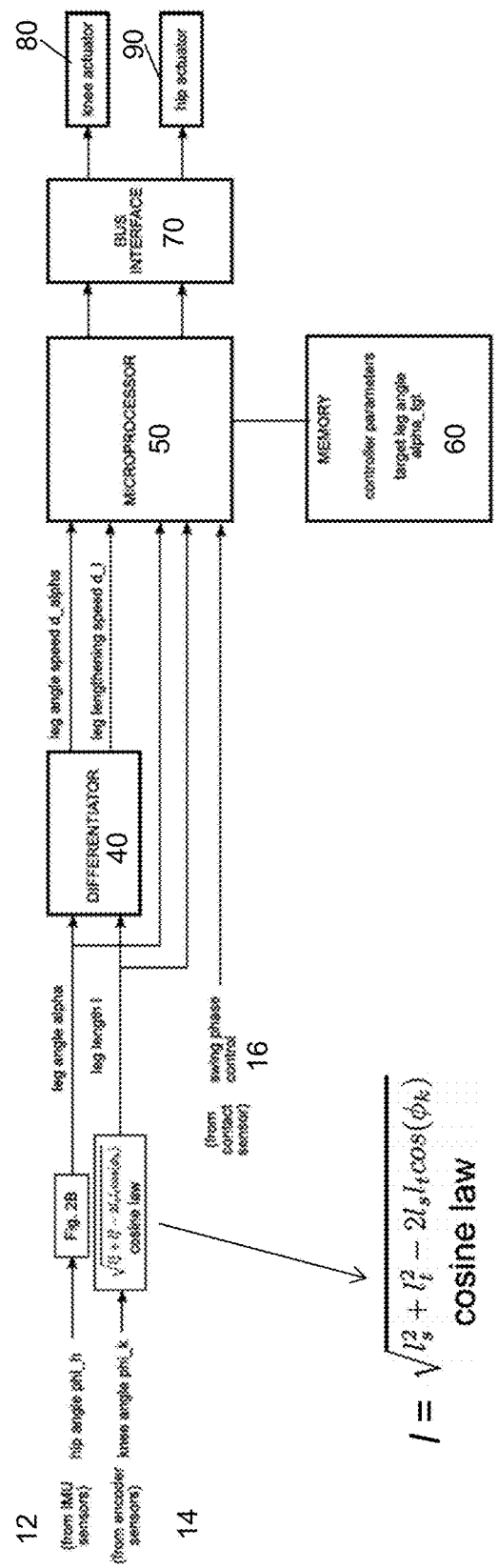
FIG. 8 is an implementation of the key modules of the system.

Now turning to FIG. 8 that illustrates an implementation of the key modules of the system. As discussed in FIG. 7, the IMU 12 determines the current hip angle $\Phi_H$ and knee encoder 14 determines current knee angle $\Phi_K$. Current leg angle $\Phi_H$ is determined from FIG. 2B based on the current leg angle $\alpha$. Current leg length 1 is calculated from the Cosine Law based on the current knee angle $\Phi_K$. The calculated current leg angle $\alpha$ and current leg length 1 are input into Differentiator 40 to determine the current leg angular speed $\dot{\alpha}$ and leg lengthening speed. Memory 60, in communication with microprocessor 50, stores the controller parameters and the target leg angle $\alpha_{tgt}$. Microprocessor 50 uses the stored data in memory 50, current hip angle $\Phi_H$, current knee angle $\Phi_K$, current leg length 1, and current leg angle $\alpha$ along the state of the swing phase based on the contact sensor in communication with the swing phase control 16 to determine the positive or negative torques to apply to knee actuator 80 and hip actuator 90 throughout the swing phase to place the foot on to the target position.

Figure 9:
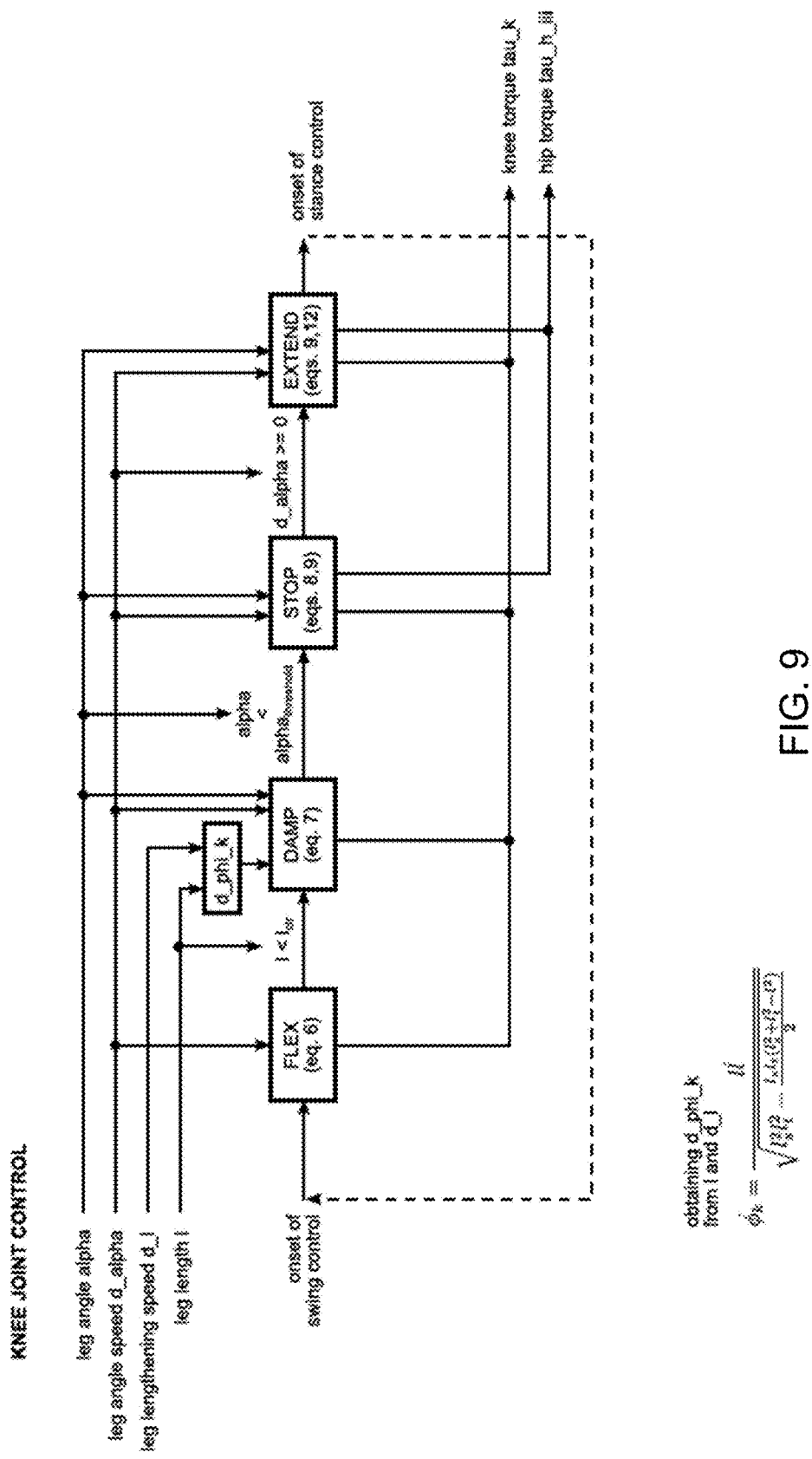
FIG. 9 is a system schematic of the knee joint control system of the present invention.

Now turning to FIG. 9 that illustrates a system schematic of the knee joint control system of the present invention. There are four phases of the typical swing phase for the knee: Flex, Damp, Stop, and Extend. The onset of the swing control is initiated when the foot is no longer in contact with the ground. Current leg angular speed $\dot{\alpha}$ (also known as leg angle speed) is input into the Flex phase that utilizes Eq. 6 for active knee flexion control applying the appropriate knee torque (no hip torque) until the current leg length 1 is less than or equal to clearance leg length $l_{clr}$. The Damp phase, which follows the Flex phase, uses as input into Eq. 7 current leg angle $\alpha$, current leg angular speed $\dot{\alpha}$, current leg length and current leg lengthening speed to apply the appropriate knee torque (no hip torque) until current leg angle $\alpha$ is less than leg angle threshold $\alpha_{threshold}$. The Stop phase, which follows the Damp phase, uses as input into Eqs. 8 and 9 current leg angle $\alpha$ and current leg angular speed $\dot{\alpha}$ to apply the appropriate knee torque (Eq. 8) and hip torque (Eq. 9) until current leg angular speed $\dot{\alpha}$ is equal to or greater than zero. The Extend phase, which follows the Stop phase, uses as input into Eqs. 9 and 12 current leg angle $\alpha$ and current leg angular speed $\dot{\alpha}$, to apply the appropriate hip torque (Eq. 9) and knee torque (Eq. 12) until the foot contacts the ground activating the contact sensor indicating the end of the swing phase and the beginning of the stance phase.

Figure 10:
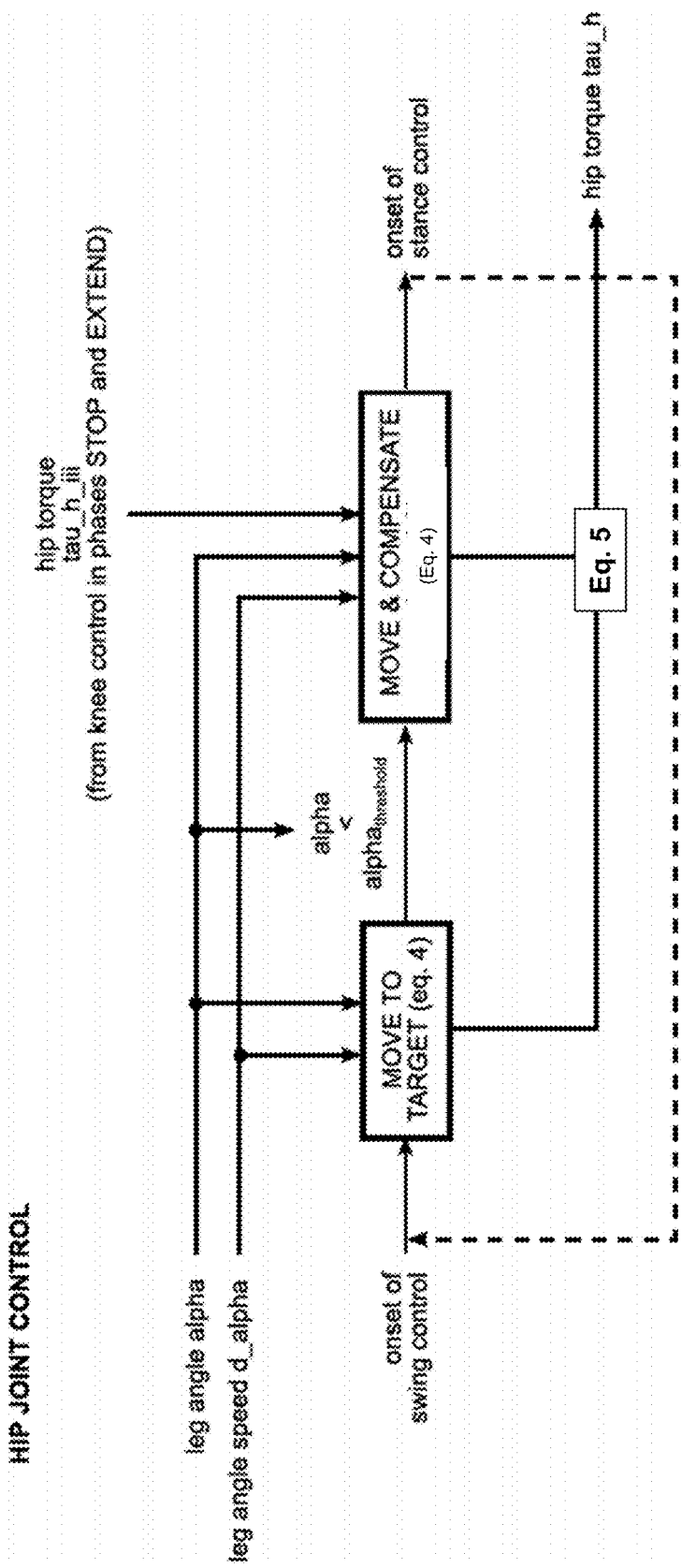
FIG. 10 is a system schematic of the hip joint control system of the present invention.

FIG. 10 is a system schematic of the hip joint control system of the present invention. As mentioned above, the onset of the swing control is initiated when the foot is no longer in contact with the ground. There are two phases of the typical swing phase for the hip: Move to Target (which is coincident with the Flex and Damp phases of the knee joint control) and Move & Compensate (which is coincident with the Stop and Extend phases of the knee joint control). The Move to Target phase uses as input into Eq. 4 current leg angle $\alpha$ and current leg angular speed $\dot{\alpha}$ to apply the appropriate hip torque until current leg angle $\alpha$ is less than leg angle threshold $\alpha_{threshold}$. The Move & Compensate phase, which follows the Move to Target phase, uses as input into Eq. 4 current leg angle $\alpha$ and current leg angular speed $\dot{\alpha}$ to calculate specific control input $\tau_h^\alpha$ and uses as input into Eq. 9 compensating torque $\tau_h^{iii}$ to calculate compensation torque. These torques are added to determine the resultant torque (Eq. 5) to apply the appropriate hip torque $\tau_h$ until the foot contacts the ground activating the constant sensor, indicating the end of the swing phase and the beginning of the stance phase.

Figure 11:
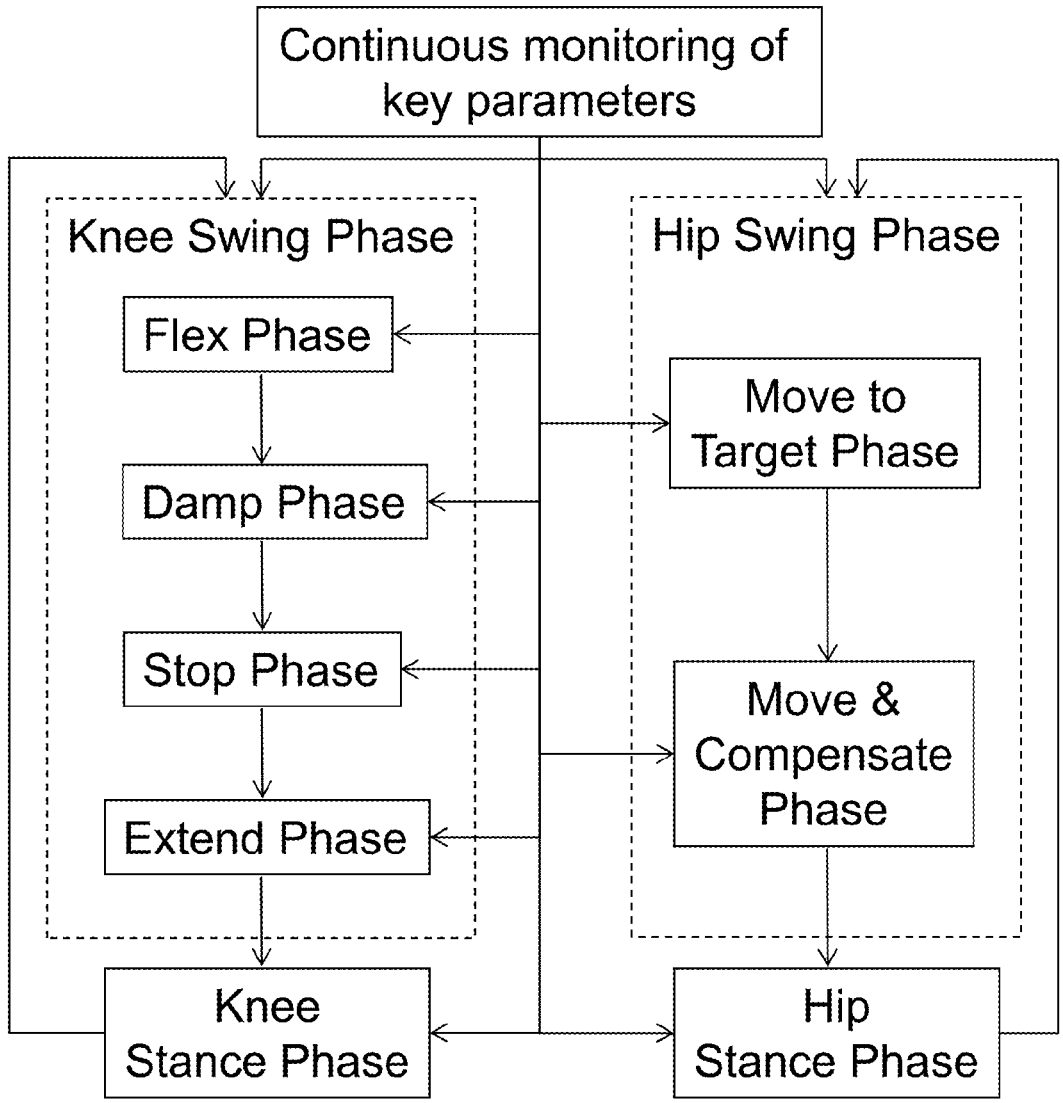
FIG. 11 is a logic flow diagram of one embodiment of the present invention.

Now turning to FIG. 11 for a logic flow diagram of one embodiment of the present invention discussed above. The present invention monitors key parameters including, but not limited to, those parameters listed in this application. The knee swing phase is independent from the hip swing phase. The knee swing phase includes the flex phase, damp phase, stop phase, and extend phase. The hip swing phase includes the Move to Target Phase and the Move & Compensate phase. The knee and hip swing phases begin when the foot leaves the ground as monitored by contact sensors. The knee and hip stance phases begin when the foot contacts the ground as monitored by contact sensors. The swings phases begin again when the foot leaves the ground.

Neuromuscular Control Model

Figure 12:
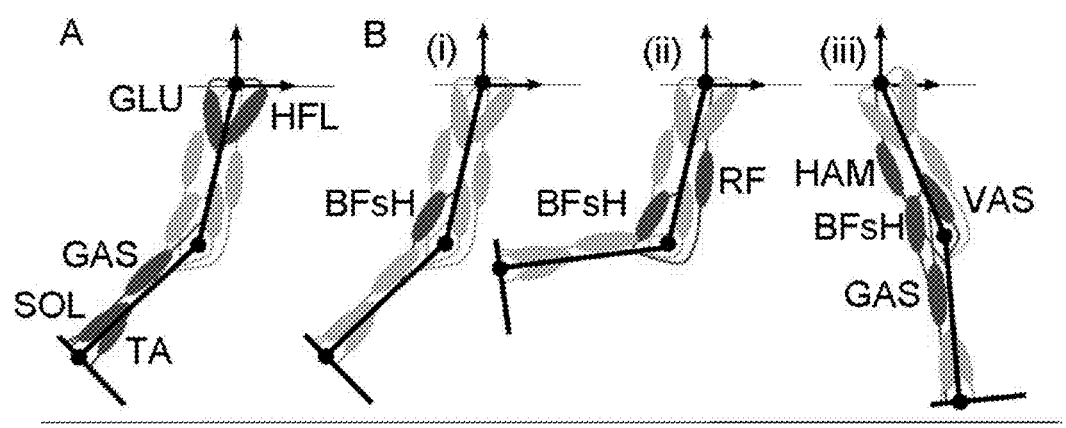
FIGS. 12A-B illustrates the neuromuscular model for swing leg placement. (A) The ankle is controlled by the soleus (SOL), gastrocnemius (GAS), and tibialis anterior (TA) muscles. The hip is flexed and extended by monoarticular hip flexor (HFL) and glutei (GLU) muscle groups. (B) The knee control is divided into the three tasks of the previously identified control. (i) Initial flexion is generated by the monoarticular biceps femoris short head muscle (BFsH). (ii) The knee is constrained by rectus femoris (RF) during hyperflexion and by BFsH during extension. (iii) The hamstring muscle group (HAM) and the vastii group (VAS) brake and extend the leg. In addition, HAM recruits GAS and BFsH to prevent knee hyper-extension.

To compare the identified control with human swing leg behavior at the level of muscle activations, and to prepare a transfer to artificial powered legs that can react like human limbs, a neuromuscular model of the human leg in swing was developed to embody the modular control with local muscle reflexes. In one embodiment, the model comprises three segments connected by revolute joints. The segments have anthropomorphic mass and inertia properties and the joints represent hip, knee and ankle. Nine Hill-type muscle models span these joints, each consisting of a contractile element CE, and parallel and series elasticities (FIG. 12). A muscle produces the net force $$F^m = F_{max}^m f_l f_v A^m$$

that is dependent on its maximum isometric force $F_{max}^m$, the force-length ($f_l$) and force-velocity relationships ($f_v$) of the contractile element, and the muscle activation $A^m$. The muscle force translates into the joint torque contribution $\tau_j^m = F^m r_j^m$ at the joints j the muscle spans, where $r_j^m$ is the muscle moment arm. The activation is related to the neural stimulation $S_m \in [0,1]$ of a muscle by $$\dot{A}^m = (S^m - A^m)/\tau_{ecc},$$

where the constant $\tau_{ecc} = 10$ ms describes the excitation-contraction coupling of muscle tissue.

For the muscle reflex embodiment of the modular leg placement control described in paragraphs the muscle stimulations are generated by local proprioceptive feedbacks from the same or other muscles (general index n), $$S^m(t) = S_0^m + \sum_n G_n^m P_n^m(t - \Delta t_n^m), \quad (13)$$

where $S_0^m$ is the muscle prestimulation, $G_n^m$ is a feedback gain, $P_n^m$ is the proprioceptive signal, $\Delta t_n^m$ represents the neural transport delay, and the sum symbol describes $\alpha$-motoneurons which can combine multiple feedbacks to generate the muscle net stimulation. The proprioceptive signals $P_n^m$ are either length or velocity signals from the originating muscle n with $$L_n^m = l_{ce}^n - l_{off}^n$$

and $$V_n^m = v_{ce}^n - v_{off}^n, \quad (14)$$

respectively. The offset values $l_{off}^n$ and $v_{off}^n$ model set point adjustments that γ-motoneurons can generate at muscle spindles, the sensory organs which measure muscle length and velocity. Note that the muscle stimulation (Eq. 13) is saturated between zero and one, reflecting that neurons modulate signals with firing rates that cannot become negative.

A. Leg Angle Estimation with Biarticular Muscle Stretch

The control described in the previous section requires the leg angle as a main input. This quantity can be estimated in the human neuromuscular system by the length of two biarticular muscles, the hamstring (HAM) and the rectus femoris (RF). Both muscles span the hip and knee. HAM is a hip extensor and knee flexor while RF flexes the hip and extends the knee. The lengths of the two muscles are given by $$l^m = l_0^m \pm r_h^m(\phi_h - \phi_{h,r}^m) \mp r_k^m(\phi_k - \phi_{k,r}^m) \quad (15)$$

where $l_0^m$ is the muscle rest length that is reached at the leg configuration defined by $\phi_{h,r}^m$ and $\phi_{k,r}^m$ and $r_h^m$ and $r_k^m$ are muscle moment arms at the hip and knee, respectively (top/bottom version for RF/HAM). In humans, $r_k^m \approx r_h^m/2$ for RF and HAM, and the leg angle relates to the hip and knee angles by $\alpha \approx \phi_h - \phi_k/2$. Equation 15 thus simplifies to $$l^m = l_0^m \pm r_h^m(\alpha - \alpha_r^m)$$

with $\alpha_r^m = \phi_{h,r}^m - \phi_{k,r}^m/2$. On the other hand, in muscle $l^m = l_{ce}^m + l_{se}^m$. Assuming that the series elasticity does not stretch substantially beyond its slack length ($l_{sl}^m$) in these muscles, $l_{se}^m \approx l_{sl}^m$ (due to the low forces required in swing), the leg angle resolves to $\alpha = \pm(l_{ce}^m + l_{sl}^m - l_0^m)/r_h^m + \alpha_r^m$. Now, the control described above requires leg angle inputs only as differences $\alpha - \alpha_i$ with respect to target values $\alpha_i$, which resolves to $$\alpha - \alpha_i = \pm 1/r_h^m (l_{ce}^m - l_{off}^m) \quad (16)$$

when choosing the offset $l_{off}^m = \pm r_h^m(\alpha_i - \alpha_r^m) - l_{sl}^m + l_0^m$, Equation (16) describes a muscle spindle length feedback (Eqs. 13 and 14) of either the RF or the HAM. Likewise, the leg angular speed can be estimated by the spindle velocity feedback of these biarticular muscles, $$\dot{\alpha} = \pm 1/r_h^m(v_{ce}^m - v_{off}^m) \text{ with } v_{off}^m = 0. \quad (17)$$

B. Ankle Control

For the control of the added ankle, the same muscles and reflexes as in conventional prosthetic ankles are used. Three muscles actuate the ankle, the monoarticular soleus (SOL) and tibialis anterior (TA) muscles as well as the biarticular gastrocnemius muscle (GAS) (FIG. 12A). While the ankle extensors SOL and GAS do not actively contribute to ankle control in swing, TA gets stimulated by its own length feedback $S^{TA} = S_0^{TA} + G_{TA}^{TA} L_{TA}^{TA}$ lifting the foot segment into the neutral position (right angle with the shank). The parameter values for all gains and offsets are reported in Table 2.

C. Hip Control

The hip portion of the modular control (Eq. 5) was implemented by stimulating the hip extensor (gluteus group, GLU) and the hip flexor (HFL) (FIG. 3A), using the stretch feedback from RF for HFL and from HAM for GLU, $$S^{HFL}(t) = S_0^{HFL} + G_{RF}^{HFL} L_{RF}^{HFL}(t - \Delta t_{RF}^{HFL}), \quad (18)$$

$$S^{GLU}(t) = S_0^{GLU} + G_{HAM}^{GLU} L_{HAM}^{GLU}(t - \Delta t_{HAM}^{GLU}), \quad (19)$$

We thus separate the flexion and extension part of the commanded torque in (Eq. 5) observing that muscle can only pull in general and that HAM and RF in particular can go slack when the leg points backward and forward, respectively. Due to (Eq. 16), the two stretch feedbacks jointly represent the first term in (Eq. 5). We do not implement the second term with explicit neuromuscular control since the muscles' force-velocity relationship automatically realizes a damping behavior. We detail how we realize the last, knee-hip-interaction term of (Eq. 5) in the next section on knee control.

TABLE 2

Control parameter values. Other parameters are known by those skilled in the art.

| Gains | | | | Offsets | |
|---|---|---|---|---|---|
| $G_{TA}^{TA}$ | 25 | $G_{BFsH}^{BFsH}$ | 1.25 | $l_{off}^{RF}$ | 0.059 (m) |
| $G_{RF}^{HFL}$ | 0.5 | $G_{HAM}^{HAM}$ | 2 | $l_{off}^{HAM}$ | 0.0716 (m) |
| $G_{HAM}^{GLU}$ | 0.5 | $G_{HAM}^{BFsH}$ | 3 | $l_{off}^{VAS}$ | 0.0324 (m) |
| $G_{RF}^{BFsH}$ | 0.1 | $G_{HAM}^{GAS}$ | 2 | $l_{off}^{TA}$ | 0.0432 (m) |
| $G_{VAS}^{RF}$ | 0.14 | $G_{VAS}^{VAS}$ | 0.05 | $S_{thr}$ | 0.65 |

D. Knee Control

The neuromuscular embodiment of the knee control follows along with the three natural control tasks. We realize the first task by stimulating the short head of biceps femoris (BFsH), a monoarticular knee flexor, with a velocity feedback (Eq. 17) from RF, $$S^{BFsH,i}(t) = G_{RF}^{BFsH} V_{RF}^{BFsH}(t - \Delta t_{RF}^{BFsH}), \quad (20)$$

using $v_{off}^{RF=0}$ (FIG. 12B). The zero offset automatically generates the velocity condition in (Eq. 6) as the resulting muscle stimulation is bound to positive values.

For the second control task, we implement a length feedback $L^{VAS}$ of the vasti (VAS), a group of monoarticular knee extensors. This feedback has no target muscle; it monitors leg length and engages the reflexes for the second task once the leg achieves sufficient ground clearance $1 < l_{clr}$. (In humans, $1 \propto \phi_k$ and $\phi_k - \phi_{k,i} = \mp 1/r_k^m(l_{ce}^m - l_{off}^m)$ and $\dot{\phi}_k = \mp 1/r_k^m(v_{ce}^m - v_{off}^m)$ for monoarticular knee extensors/flexors). During the second task, we realize the extension part (first line of Eq. 3) by stimulating RF with a velocity feedback from VAS $$S^{RF,ii}(t) = G_{VAS}^{RF} V_{VAS}^{RF}(t - \Delta t_{VAS}^{RF}). \quad (21)$$

For the flexion part (second and third line), BFsH is simulated with its own velocity feedback, $$S^{BFsH,ii}(t) = G_{BFsH}^{BFsH} V_{BFsH}^{BFsH}(t - \Delta t_{BFsH}^{BFsH}) M, \quad (22)$$

where M are modulating reflexes with $$M = L_{RF}^{BFsH}(t - \Delta t_{RF}^{BFsH}) \cdot [V_{BFsH}^{BFsH}(t - \Delta t_{BFsH}^{BFsH}) + V_{RF}^{BFsH}(t - \Delta t_{RF}^{BFsH})].$$

The first modulation reflex from the biarticular RF implements the term $(\alpha - \alpha_{tgt})$ of (Eq. 7). The other modulation term in this equation, $(\dot{\phi}_k + \dot{\alpha})$, is implemented using the sum of two velocity reflexes from BFsH for $\dot{\phi}_k$ and from RF for $\dot{\alpha}$. These velocity reflexes also implicitly ensure the condition $\dot{\phi}_k > \dot{\alpha}$ for generating flexion torque.

The final control task of braking and extending the leg is implemented primarily by stimulating HAM and VAS (FIG. 3B). We use the biarticular stretch reflex $$S^{HAM,iii}(t) = G_{HAM}^{HAM} L_{HAM}^{HAM}(t - \Delta t_{HAM}^{HAM}) \quad (23)$$

to stimulate HAM, which mimics the term $(\alpha_{thr}\alpha\dot\alpha)$ of (Eq. 8) when using the offset value $$l_{off}^{HAM} = -r_h^{HAM}(\alpha_{thr} - \alpha_r^{HAM}) - l_{sl}^{HAM} + l_0^{HAM}.$$

In addition, HAM proportionally recruits the synonymous knee flexors BFsH and GAS once its stimulation exceeds a threshold $S^{HAM,iii} > S_{thr}$, $$S^{BFsH,iii}(t) = G_{HAM}^{BFsH}[S^{HAM,iii}(t) - S_{thr}], \quad (24)$$

$$S^{GAS,iii}(t) = G_{HAM}^{GAS}[S^{HAM,iii}(t) - S_{thr}], \quad (25)$$

to prevent hyper extension of the knee caused by HAM torque saturation at high swing leg angular speeds. The second, velocity term of (Eq. 8) is neglected in the control as the HAM's force-velocity relationship produces a similar damping behavior. However, we use a passive velocity feedback $V^{HAM}$ to monitor when the leg angular speed has slowed down to zero ($\dot\alpha=0$), which triggers VAS stimulation by its own stretch reflex, $$S^{VAS,iii}(t) = G_{VAS}^{VAS} L_{VAS}^{VAS}(t - \Delta t_{VAS}^{VAS}), \quad (26)$$

to extend the knee.

Although the muscle reflexes are introduced along with the three control tasks, they are active throughout swing without the separation into task-related phases. For instance, the total stimulation of BFsH is generated by $S^{BFsH,tot} = S^{BFsH,i} + S^{BFsH,ii} + S^{BFsH,iii}$. The only exception is the VAS extension reflex, which is connected only after $\dot\alpha=0$ in the last task.

Results and Discussion

A. Leg Placement into Arbitrary Targets

The control parameters of the neuromuscular model were tuned by hand with two goals in mind. First, with the application to autonomous prostheses in mind, a single set of parameters that minimizes the error between the landing leg angle and its target $\alpha_{tgt}$ for a large range of initial joint velocities and target angles exceeding those of human walking and running were sought after. Second, it was required that the corresponding joint torques to stay within experimentally observed ranges.

The identified set of control parameters is shown in Table 2. Except for $\alpha_{thr}$, which differs between walking and running (12/24 deg respectively), parameters remain constant. The larger threshold angle for activating HAM earlier in running than in walking is needed to prevent knee hyper-extension. Such an earlier activation is also observed in humans.

Figure 13:
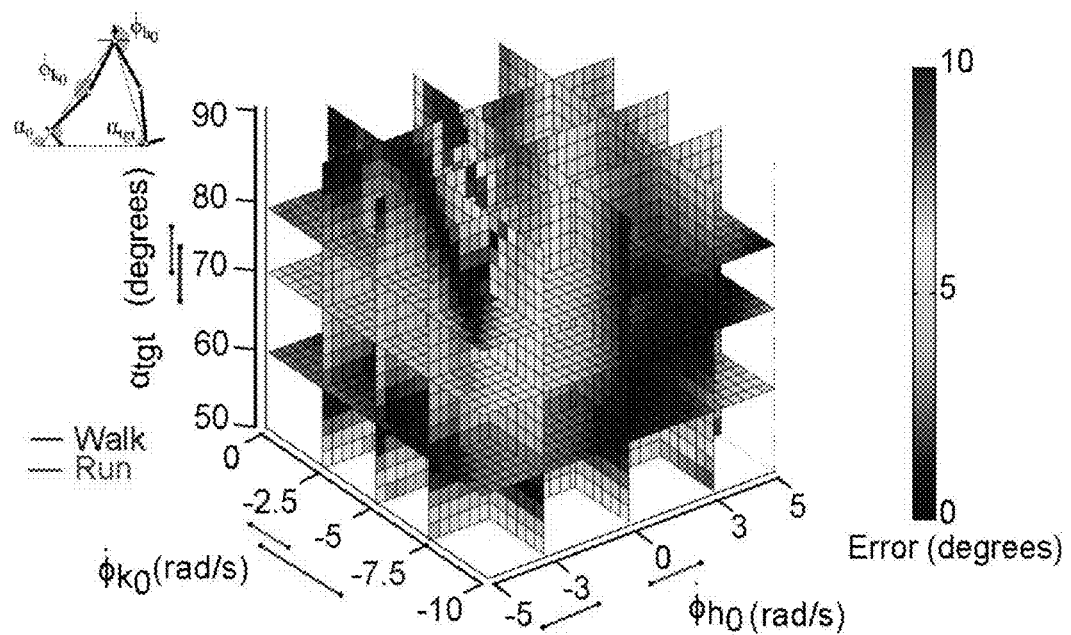
FIG. 13 illustrates the swing leg placement error for the neuromuscular control model. The leg is hinged and the initial configuration is set to $\phi_{h,0}$=220 deg, $\phi_{k,0}$=175 deg ($\alpha_0$=132.5 deg), and $\phi_{a,0}$=120 deg. The clearance leg length is set to $l_{clr}$=5 cm.

The achieved performance of target placement with the neuromuscular system is shown in FIG. 13. For target angles $\alpha_{tgt}=50 \ldots 75$ deg and for initial joint velocities $\dot\phi_{h,0}= 5 \ldots 5$ rads$^{-1}$ and $(\dot{i})_{k,0}=-10 \ldots 0$ rads$^{-1}$, the average and maximum placement errors are 2.8 deg and 9.2 deg. These errors compare with the performance of the ideal control and cover typical human landing leg angles and initial joint speeds observed in walking and running. For steeper target angles, however, the placement shows clearly larger error due to the toe dragging the ground.

B. Comparison to Human Walking and Running

In another example, the resulting swing leg motions were compared to actual human leg motions. The swing leg trajectories of a subject walking at slow to fast speeds (0.65 ms$^{-1}$ to 2 ms$^{-1}$) and running at slow to moderately fast speeds (2.5 ms$^{-1}$ to 5.5 ms$^{-1}$) were recorded. The subject's ankle trajectories and corresponding hip and knee torques during swing are shown in the left column of FIGS. 14A-F. The right column shows the patterns predicted by the neuromuscular model. (Note that for the comparison the observed hip translational accelerations and leg initial conditions were applied to the model.) In addition, FIGS. 16A-C compare the time history of muscle activations generally observed in walking and running with those predicted by the model for matched speeds.

Figure 14:
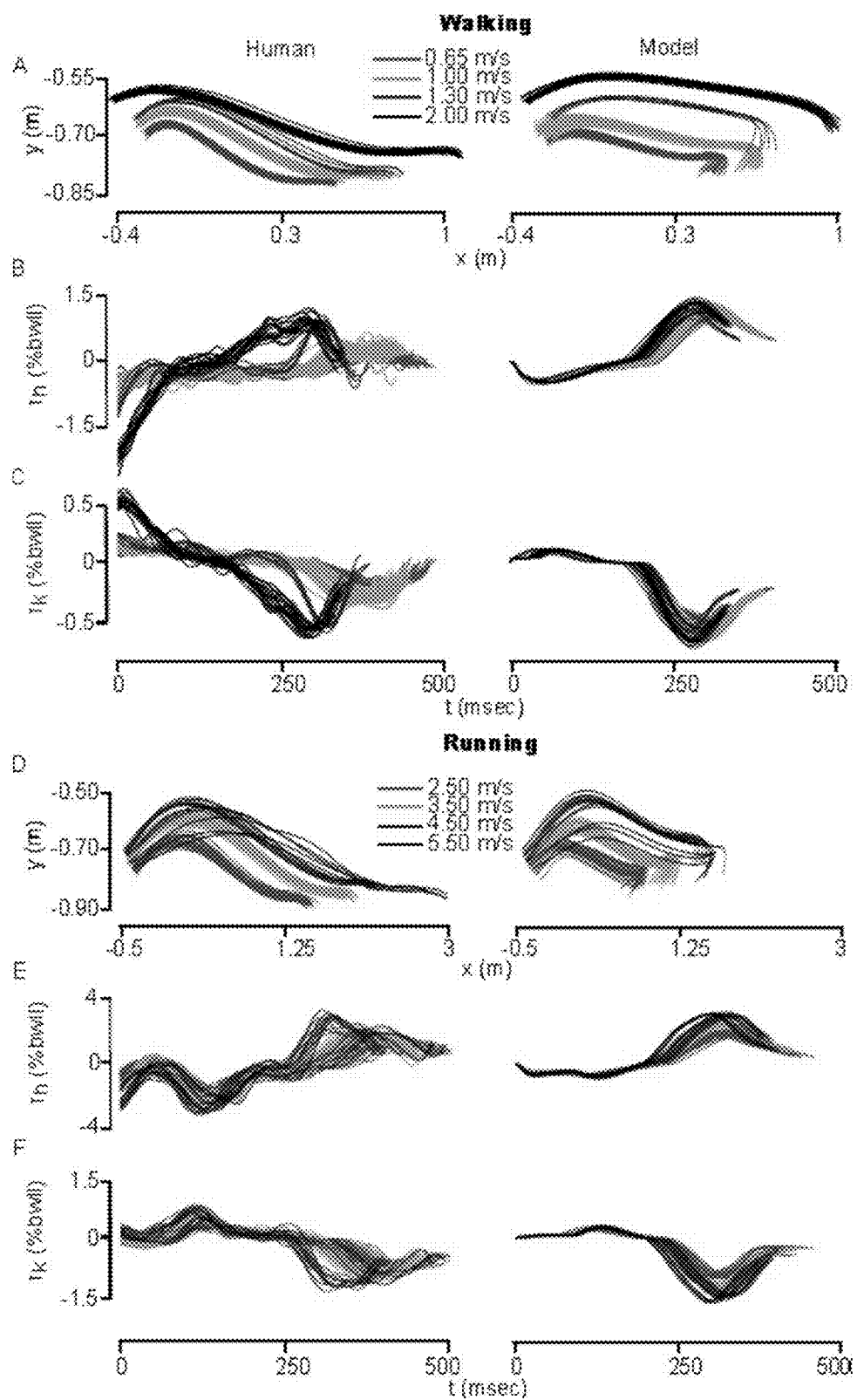
FIGS. 14A-F show the observed and predicted swing leg patterns in walking and running. The ankle trajectories (A,D), hip and knee torques (B,C,E,F) of multiple swing phases (individual traces) are compared between human and model at different speeds (color coded). For the model, the initial joint positions and speeds as well as the hip translational accelerations are taken from the corresponding human swing motions. The target angle is set to the observed (average) landing angle $\alpha_{tgt}$=70 deg. The ankle trajectories are given with respect to a world frame that originates at the initial position of the hip. The torques are normalized to percent of body weight times leg length (% bwll)
Figure 15:
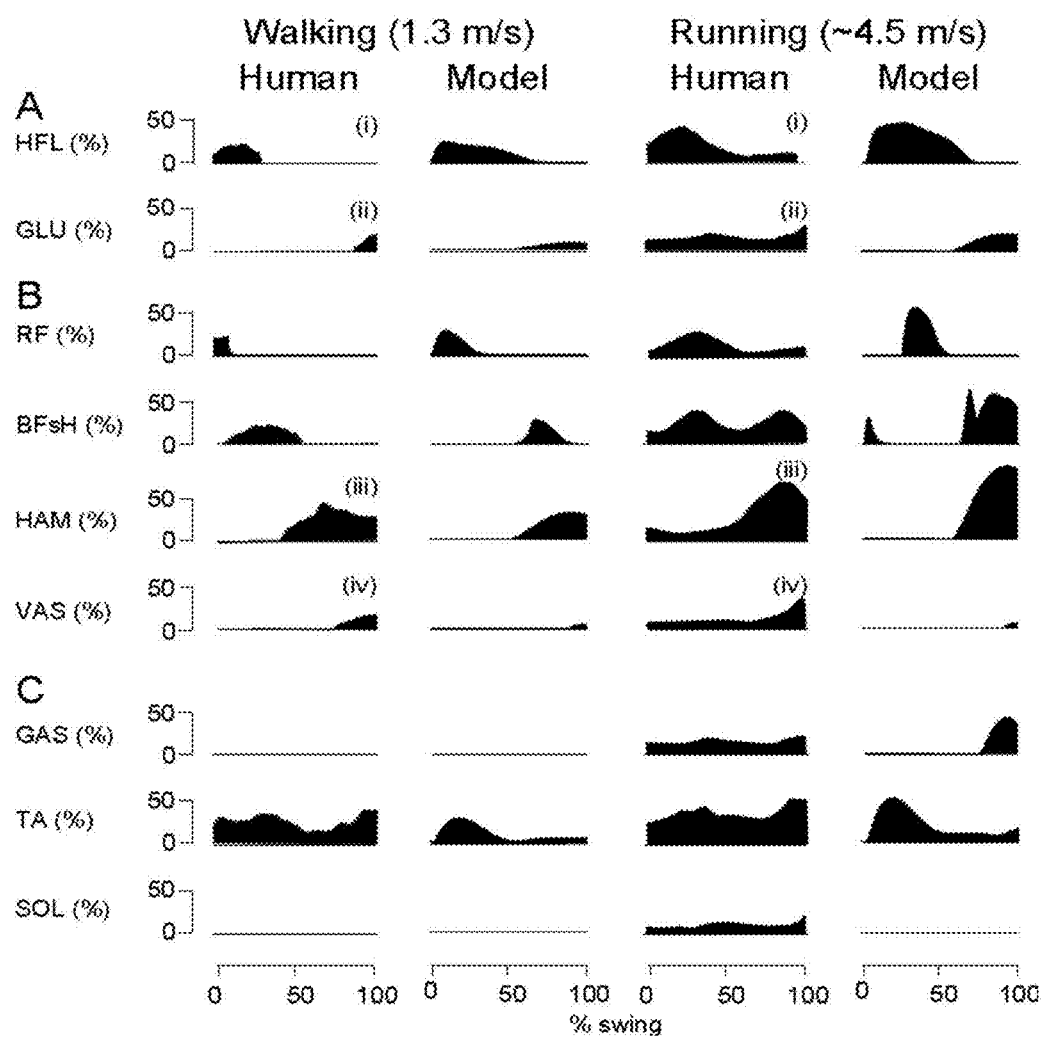
FIGS. 15A-C show the observed and predicted muscle activations in walking and running. Steady-state patterns of muscle activations during swing are shown for hip (A), knee (B) and ankle muscles (C). Compared muscles: (i) iliacus (ii) upper gluteus maximum, (iii) semimembranosis, and (iv) vastus lateralis.

In walking, the swing leg patterns predicted by the model are similar to the ones observed in humans. The ankle trajectories have a similar range and shape in particular for slower walking speeds (FIG. 14A), and the hip and knee torques have similar magnitudes and gross behavior except for the larger initial torques in human walking at 2 ms$^{-1}$ (FIGS. 14B and 14C). The activation patterns for the hip muscles HFL and GLU show similar timings and magnitudes between the model and humans (FIG. 15A). Although the knee muscle activation patterns show a similar trend (FIG. 15B), some deviations occur with respect to the onset time for BFsH, which is delayed. For the ankle muscles, TA misses the late swing activation seen in humans in preparation for stance (FIG. 15C), a known shortcoming of an example ankle control.

In contrast to walking, the patterns for running show more deviations between the model and humans. The model has a shorter stride length and a clearly faster swing time than present in human running (FIG. 14D). Despite these differences, the shapes of the torque patterns match human data in general (FIGS. 14E and 14F). In the activation patterns, humans have an increased tonus for all muscles that is absent in the model (FIGS. 15A-C). In addition to this muscle tonus, the activities of BFsH and GAS show different characteristic features. In humans, BFsH has a prominent activation peak that coincides with RF peak activation (FIG. 15B). By contrast, in the model, the early BFsH peak occurs at the very beginning of swing and RF activity onset is delayed. Further, the model shows an activation burst of GAS at the end of swing due to the synonymous activation (Eq. 25) that humans do not seem to have to such an extent (FIG. 15C).

FIGS. 16-24 describe example implementation of the swing leg controller (FIG. 7) with an algorithm that emulates human neuromuscular control, taking sensory input about hip and knee angles as well as swing phase detection and converting this input into hip and knee joint torque commands.

Figure 16:
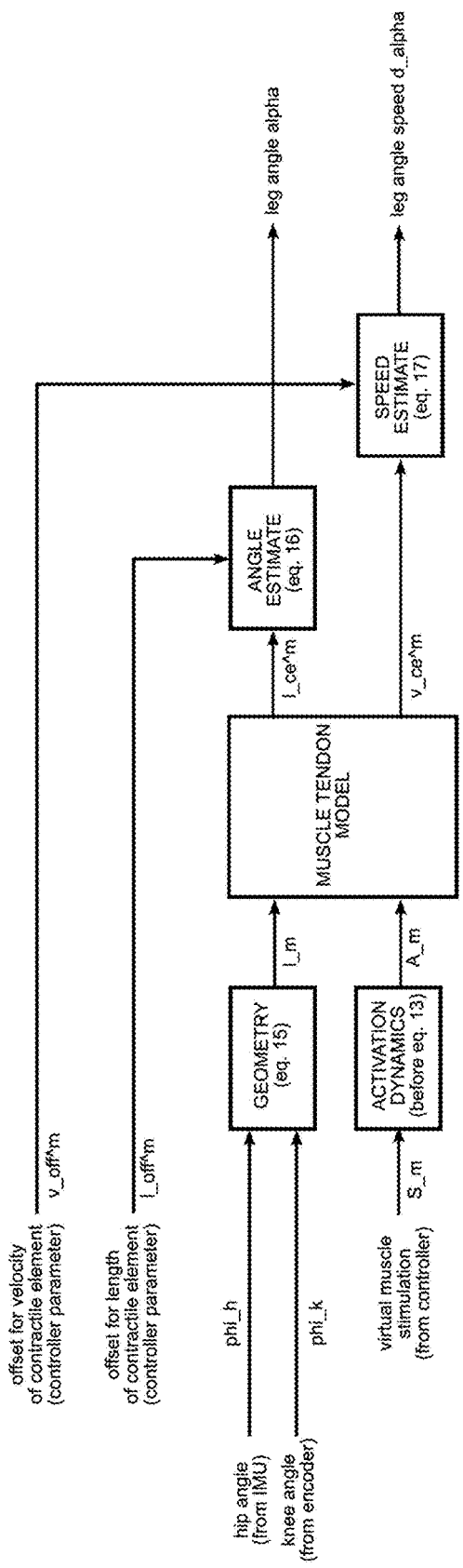
FIG. 16 is an overview of one aspect of the neuromuscular control model of the present invention illustrating the process for neuromuscular estimates of leg angle and leg angular speed.
Figure 17:
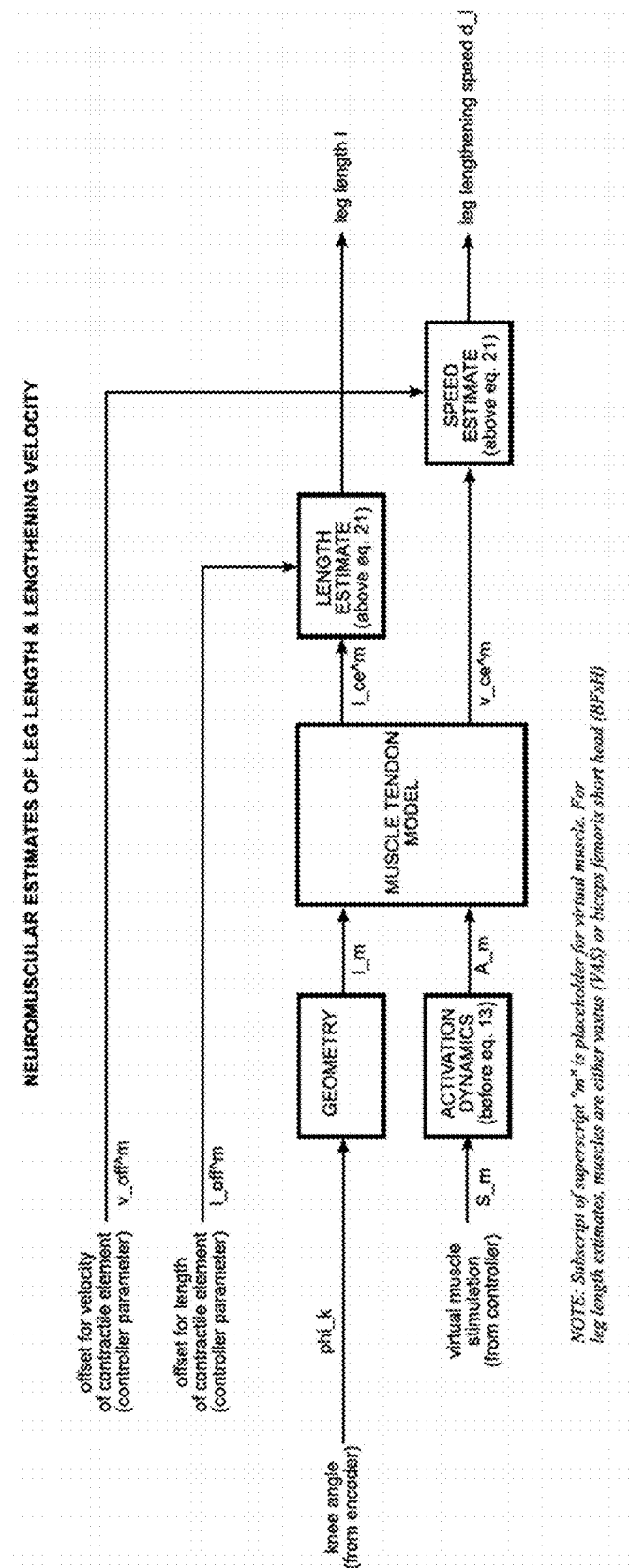
FIG. 17 is an overview of another aspect of the neuromuscular control model of the present invention illustrating the process for neuromuscular estimates of leg length and leg lengthening speed.

FIGS. 16 and 17 describe how the algorithm translates sensor inputs from an IMU (hip angle) and a knee encoder (knee angle) into estimates of leg angle and leg angular speed (FIG. 16) as well as leg length and leg lengthening speed (FIG. 17).

In FIG. 16, joint angle information from the hip and knee sensors is converted into the length of a virtual muscle that spans both joints (GEOMETRY). This virtual muscle represents either the hamstring (HAM) or the rectus femoris (RF). Together with a virtual muscle stimulation that is provided by the algorithm described in FIG. 18 and gets converted into muscle activation (ACTIVATION DYNAMICS), the resulting muscle length and velocity is computed (MUSCLE TENDON MODEL). From this virtual muscle length and velocity information, the current leg angle (ANGLE ESTIMATE) and current leg angular speed (SPEED ESTIMATE) of the swing leg are estimated. The offsets for the muscle length (l_off^m) and velocity (v_off^m) are control parameters of the algorithm and provided by the designer.

In FIG. 17, joint angle information from the knee sensor is converted into the length of a virtual muscle that spans the knee joint (GEOMETRY). This virtual muscle represents either the vastii group (VAS) or the biceps femoris short head (BFSH). Together with a virtual muscle stimulation that is provided by the algorithm described in FIG. 18 and gets converted into muscle activation (ACTIVATION DYNAMICS), the resulting muscle length and velocity is computed (MUSCLE TENDON MODEL). From this virtual muscle length and velocity information, the current leg length (LENGTH ESTIMATE) and current leg lengthening speed (SPEED ESTIMATE) of the swing leg are estimated. The offsets for the muscle length ($l\_off\hat{\ }m$) and velocity ($v\_off\hat{\ }m$) are control parameters of the algorithm and provided by the designer.

Figure 18:
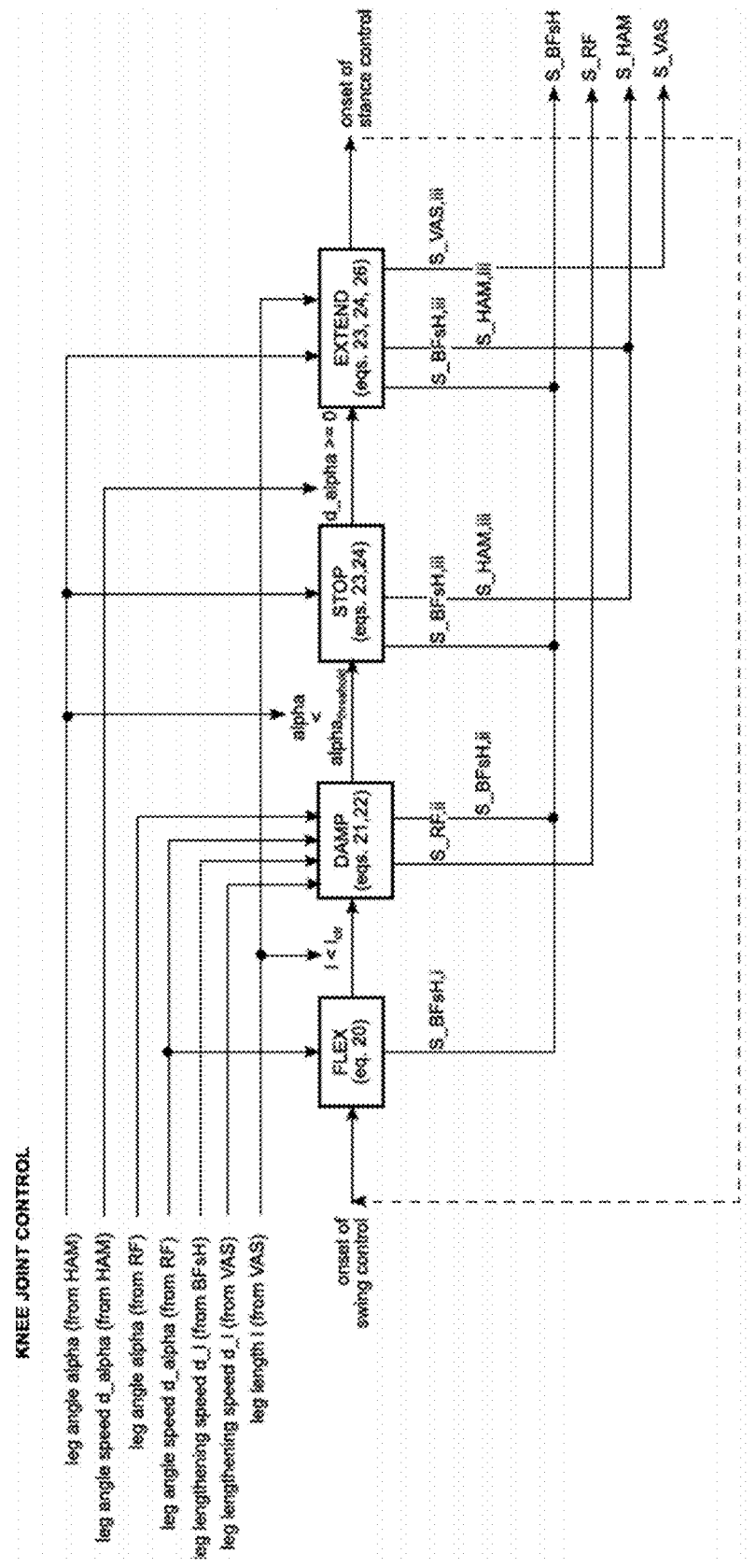
FIG. 18 is an overview of yet another aspect of the neuromuscular control model of the present invention illustrating the process for knee joint control.
Figure 19:
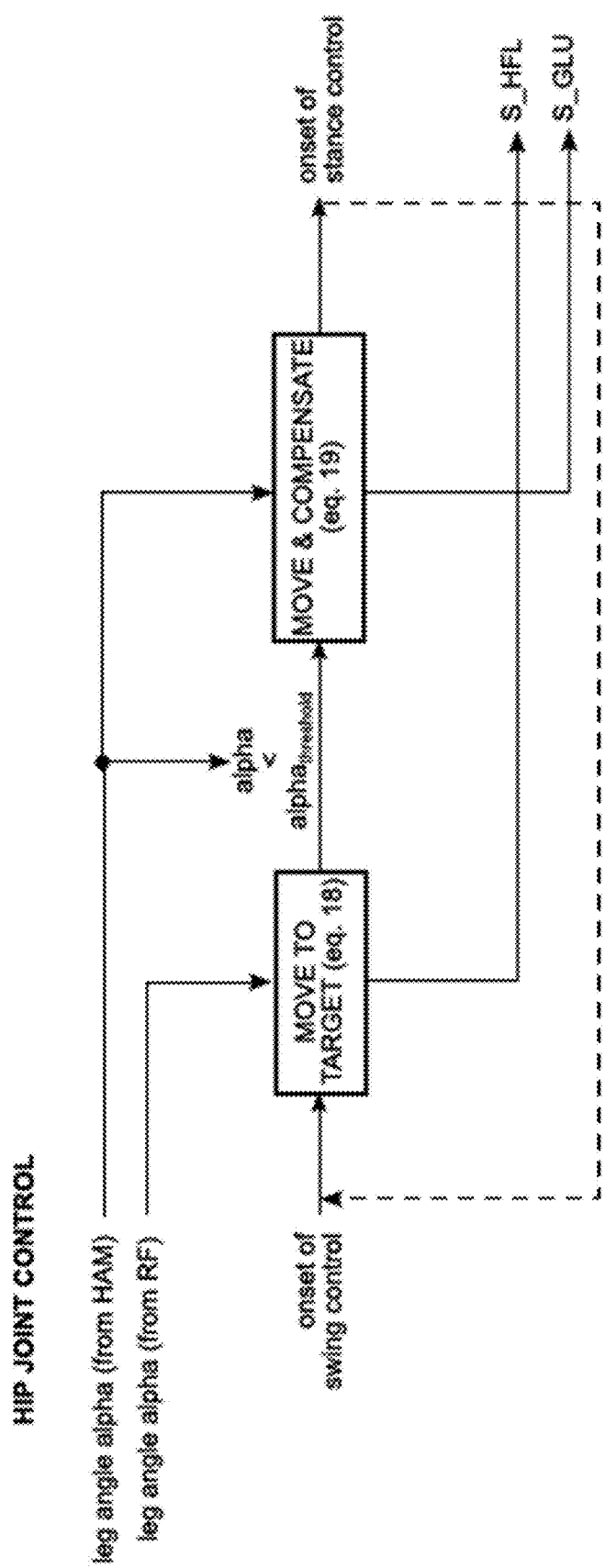
FIG. 19 is an overview of yet another aspect of the neuromuscular control model of the present invention illustrating the process for hip joint control.

FIGS. 18 and 19 describe how the algorithm converts the estimates of leg angle, leg angular speed, leg length, and leg lengthening speed into muscle stimulations $S\_m$ of six virtual leg muscles m (BFSH, RF, HAM, GAS, VAS, HFL, GLU). These muscle stimulations contribute in a virtual feedback loop to the generation of the estimates of leg angle, leg angular speed, leg length, and leg lengthening speed (FIGS. 16 and 17). The muscle stimulation signals are also used to compute hip and knee torques contributed by the individual muscles (FIGS. 20, 21 and 22).

FIG. 18 shows a schematic of this conversion for the knee joint control. The conversion is separated into the four control phases described in FIG. 9. The initial FLEX phase engages when the swing phase sensor detects the onset of swing. In the FLEX phase, the estimate of leg angular speed d_alpha using the virtual muscle RF is used to generate the muscle stimulation of the virtual muscle BFSH according to equation 13. The estimate of leg length l using the virtual muscle VAS is used during this phase to continuously check if the leg length has contracted below the clearance length l_clr (FIG. 2C). Once l<l_clr, the algorithm enters the DAMP phase, and virtual muscle stimulations of RF and BFSH are computed according to equations 14 and 15 using the estimate of leg lengthening speed from VAS and BFSH (FIG. 17), and the estimate of leg angle and leg angular speed from RF (FIG. 16). Throughout the DAMP phase, the estimate of the leg angle using the virtual muscle HAM (FIG. 16) is used to continuously check if the leg angle alpha is below the threshold alpha_threshold (FIG. 2C). Once alpha<alpha_threshold, the algorithm enters the STOP phase. In the STOP phase, the estimate of the leg angle alpha using HAM (FIG. 16) is used to compute the stimulation of HAM according to equation 16. In addition the resulting HAM stimulation is used to compute the stimulation of BFSH according to equation 17. Throughout the STOP phase, the estimate of the leg angle velocity using the virtual muscle HAM (FIG. 16) is used to continuously check if the leg angle velocity d_alpha has reversed to positive values (FIG. 2C). Once d_alpha>=0, the algorithm enters the EXTEND phase, and the stimulations of the virtual muscles BFSH, HAM and VAS are computed according to equations 16, 17 and 19 using the estimate of leg angle from HAM (FIG. 16) and the estimate of leg length from VAS (FIG. 17). The EXTEND phase ends when the swing phase sensor detects the onset of stance.

FIG. 19 shows a schematic of the conversion from estimated leg angle and angular speed to virtual muscle stimulations for the hip flexor and extensor muscles (HFL and GLU). The initial MOVE TO TARGET phase starts when the swing phase sensor detects the onset of swing. During this phase, the algorithm computes according to equation 11 the stimulation of the virtual hip flexor muscle HFL using the estimate of the leg angle alpha from RF (FIG. 16). Throughout this phase, the leg angle estimate from HAM (FIG. 16) is used to continuously check if the leg angle alpha is below the threshold alpha_threshold (FIG. 2C). Once alpha<alpha_threshold, the algorithm enters the MOVE & COMPENSATE phase. In this phase, the estimate of the leg angle from HAM (FIG. 16) is used to compute the stimulation of the virtual hip extensor muscle GLU according to equation 12. The MOVE & COMPENSATE phase ends when the swing phase sensor detects the onset of stance.

Figure 20:
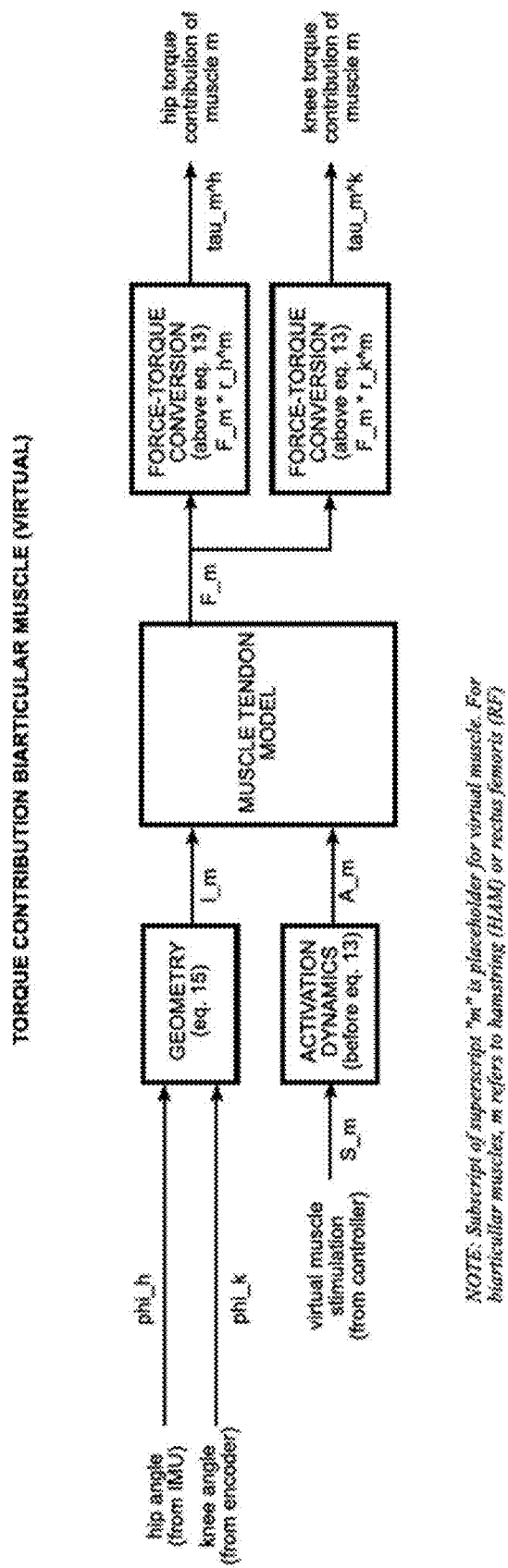
FIG. 20 is an overview of yet another aspect of the neuromuscular control model of the present invention illustrating the process for torque contribution of biarticular muscle.
Figure 21:
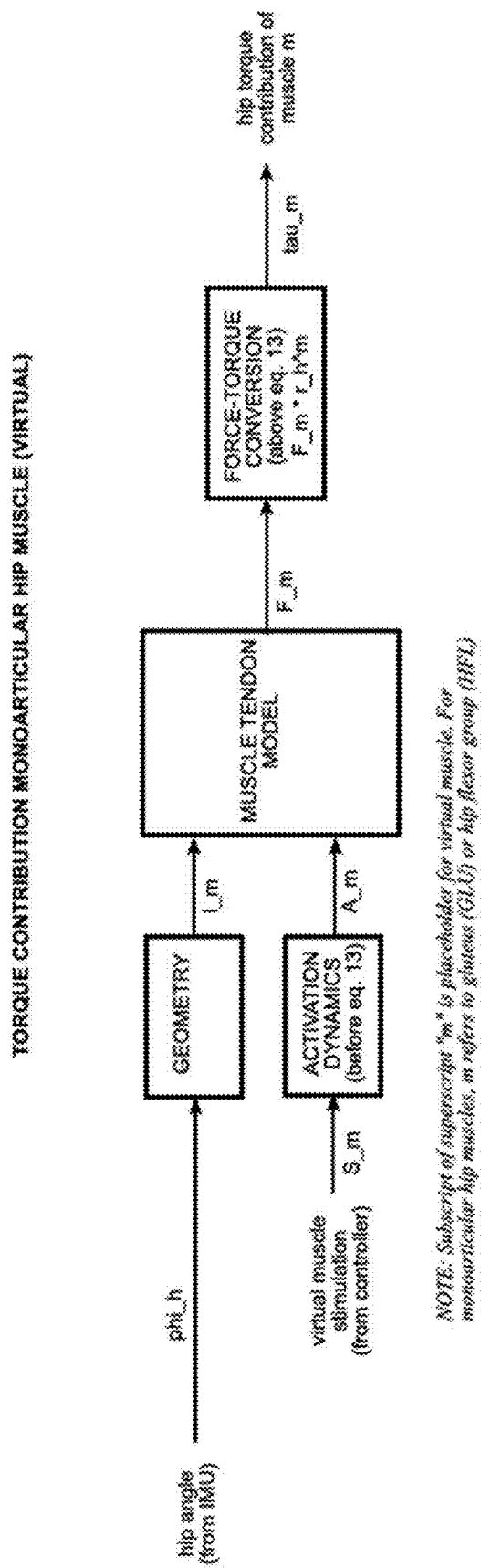
FIG. 21 is an overview of yet another aspect of the neuromuscular control model of the present invention illustrating the process for torque contribution of monoarticular hip muscle.
Figure 22:
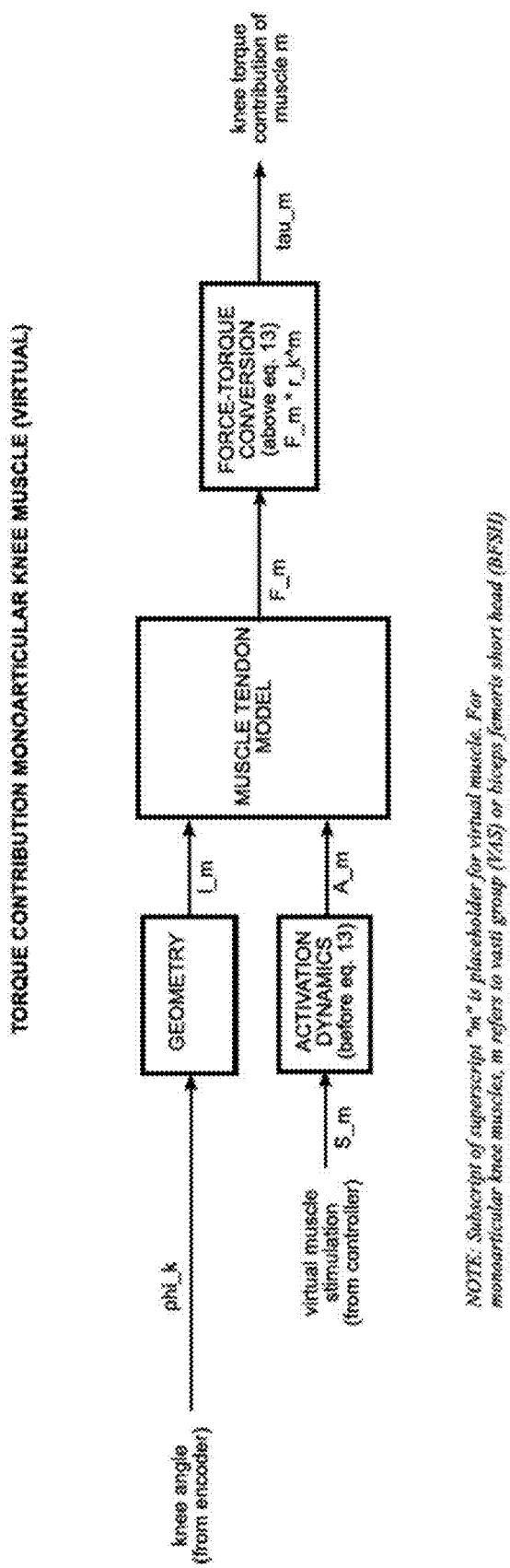
FIG. 22 is an overview of yet another aspect of the neuromuscular control model of the present invention illustrating the process for torque contribution of monoarticular knee muscle.

FIGS. 20, 21 and 22 schematically describe how the algorithm converts stimulations of the virtual muscles into desired torque contributions about the hip and knee joint by these muscles.

FIG. 20 describes this conversion for the virtual biarticular muscles (HAM and RF). Joint angle information from the hip and knee sensors is converted into the length of a virtual muscle that spans both joints (GEOMETRY). Together with a virtual muscle stimulation that is provided by the algorithm described in FIG. 18 and gets converted into muscle activation (ACTIVATION DYNAMICS), the resulting muscle force is computed (MUSCLE TENDON MODEL). This muscle force $F\_m$ is converted into torque contribution to the hip (FORCE TORQUE CONVERSION) according $tau\_m\hat{\ }h=F\_m*r\_h\hat{\ }m$. The moment arm $r\_h\hat{\ }m$ is a control parameter of the algorithm and provided by the designer. The muscle force $F\_m$ is also converted into a torque contribution to the knee (FORCE TORQUE CONVERSION) according $tau\_m\hat{\ }k=F\_m*r\_k\hat{\ }m$. The moment arm $r\_k\hat{\ }m$ is a control parameter of the algorithm and provided by the designer.

FIG. 21 describes the conversion from muscle stimulation to joint torque contribution for the virtual muscles that span only the hip (GLU and HFL). Joint angle information from the hip sensor is converted into the length of a virtual muscle that spans the hip (GEOMETRY). Together with a virtual muscle stimulation that is provided by the algorithm described in FIG. 19 and gets converted into muscle activation (ACTIVATION DYNAMICS), the resulting muscle force is computed (MUSCLE TENDON MODEL). This muscle force $F\_m$ is converted into torque contribution to the hip (FORCE TORQUE CONVERSION) according $tau\ mAh=F\_m*r\_h\hat{\ }m$. The moment arm $r\_h\hat{\ }m$ is a control parameter of the algorithm and provided by the designer.

FIG. 22 describes the conversion from muscle stimulation to joint torque contribution for the virtual muscles that span only the knee (BFSH and VAS). Joint angle information from the knee sensor is converted into the length of a virtual muscle that spans the hip (GEOMETRY). Together with a virtual muscle stimulation that is provided by the algorithm described in FIG. 18 and gets converted into muscle activation (ACTIVATION DYNAMICS), the resulting muscle force is computed (MUSCLE TENDON MODEL). This muscle force $F\_m$ is converted into torque contribution to the knee (FORCE TORQUE CONVERSION) according $tau\_m\hat{\ }k=F\_m*r\_k\hat{\ }m$. The moment arm $r\_k\hat{\ }m$ is a control parameter of the algorithm and provided by the designer.

Figure 23:
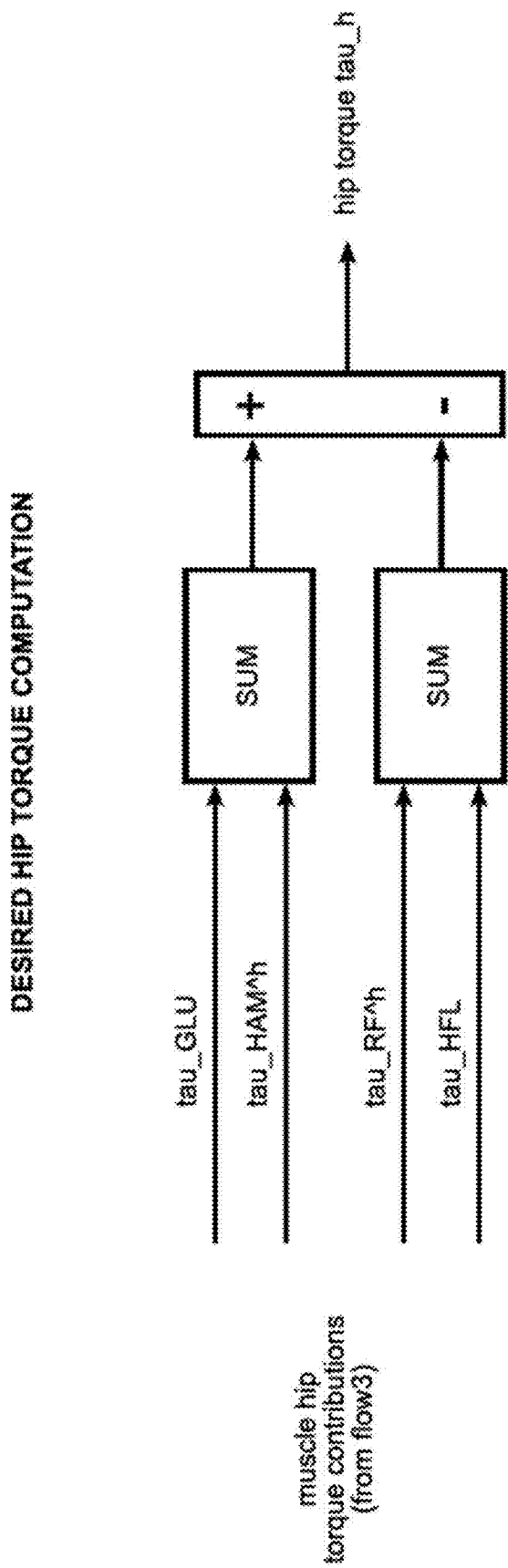
FIG. 23 is an overview of yet another aspect of the neuromuscular control model of the present invention illustrating the process for desired hip torque computation.
Figure 24:
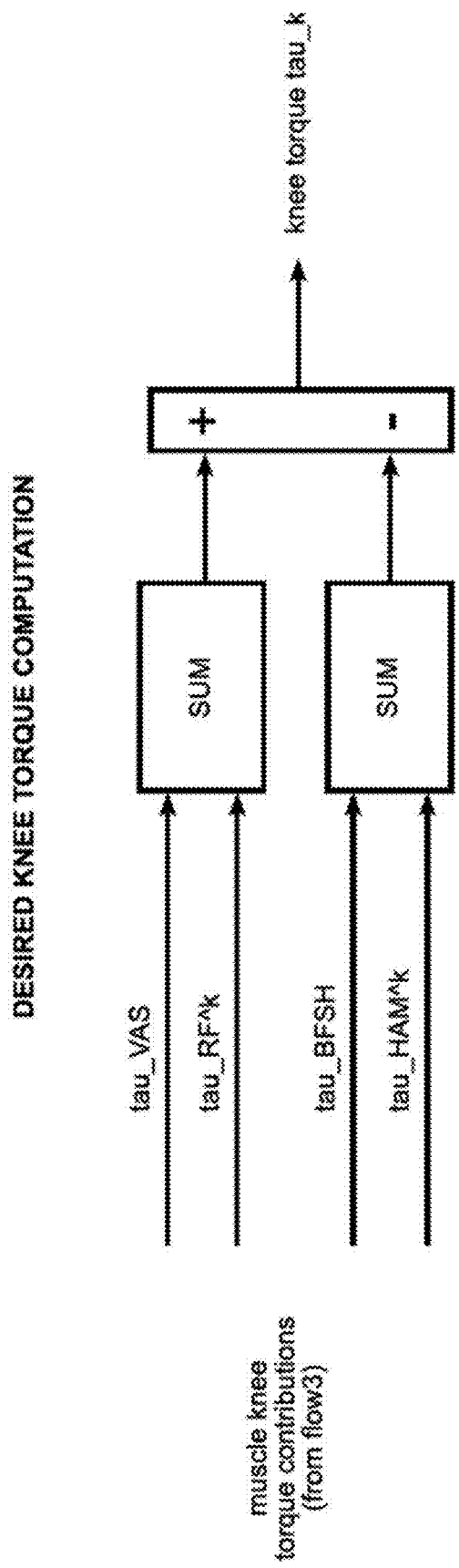
FIG. 24 is an overview of yet another aspect of the neuromuscular control model of the present invention illustrating the process for desired knee torque computation.

FIGS. 23 and 24 describe schematically how the algorithm computes desired hip and knee torques from the muscle torque contributions.

FIG. 23 shows this computation for the hip joint. The summed torque contributions of the hip flexor muscles (RF and HFL) are subtracted from the summed torque contributions of the hip extensor muscles (GLU and HAM), generating the desired hip torque tau_h of the swing leg controller.

FIG. 24 shows the computation of the desired knee joint torque. The summed torque contributions of the knee flexor muscles (BFSH and HFL) are subtracted from the summed torque contributions of the knee extensor muscles (GLU and HAM), generating the desired knee torque tau_k of the swing leg controller.

The invention claimed is:

1. A method for placing an artificial foot connected to a prosthetic or robotic limb on to a target point, wherein the method comprises:
    providing the prosthetic or robotic limb with a rotatable artificial hip joint, a rotatable artificial knee joint, an artificial thigh having length ($l_t$) coupled to the rotatable artificial hip joint and the rotatable artificial knee joint, an artificial shank having length ($l_s$) coupled to the rotatable artificial knee joint,
    providing a hip torque actuator coupled to the rotatable artificial hip joint, and a knee torque actuator coupled the rotatable artificial knee joint;
    providing a controller in communication with: i. a rotatable artificial hip joint sensor to measure a current hip rotation angle ($\phi_h$), ii. a rotatable artificial knee joint sensor to measure a current knee rotation angle ($\phi_k$), iii. the hip torque actuator to apply a positive or a negative torque to the rotatable artificial hip joint, and iv. the knee torque actuator to apply a positive or a negative torque to the rotatable artificial knee joint;
    inputting into the controller one or more parameters from the group consisting of a target leg angle ($\alpha_{tgt}$), a leg clearance length ($l_{clr}$) a proportional gain ($k_p^\alpha$), a derivative gain ($k_d^\alpha$), a stopping gain ($k^{stp}$), an extension gain ($k^{ext}$), a flexing gain ($k^i$), a damping gain ($k^{ii}$), a maximum return leg angle velocity ($\dot{\alpha}_{max}$), and a leg angle threshold delta ($\Delta\alpha_{thr}$);
    wherein the controller executes the following steps of the method:
    a. continuously measuring the current hip rotation angle ($\phi_h$) and the current knee rotation angle ($\phi_k$);
    b. continuously determining a current leg angle velocity ($\dot{\alpha}$) and a current leg angle ($\alpha$) based on the current hip rotation angle ($\phi_h$) and the current knee rotation angle ($\phi_k$);
    c. calculating the adjustable leg length (l) based on the current knee rotation angle ($\phi_k$), the thigh length ($l_t$), and the shank length ($l_s$);
    d. applying a first torque or no torque to the rotatable artificial knee joint and/or a first torque or no torque to the rotatable artificial hip joint until the adjustable leg length (l) is equal to or less than the leg clearance length ($l_{clr}$);
    e. applying a second torque or no torque to the rotatable artificial knee joint and/or a second torque to the rotatable artificial hip joint until a threshold leg angle $\alpha_{thr}$, defined as ($\alpha_{tgt}+\Delta\alpha_{thr}$), is reached;
    f. applying a third torque or no torque to the rotatable artificial knee joint and/or a third torque or no torque to the rotatable artificial hip joint until the current leg angle velocity ($\dot{\alpha}$) equal to or greater than zero; and
    g. applying a fourth torque or no torque to the rotatable artificial knee joint and/or a fourth torque or no torque the rotatable artificial hip joint until the artificial foot contacts the target point,
    whereby motion of the rotatable artificial hip joint and the rotatable artificial knee joint are determined without enforcing reference trajectories of the rotatable artificial hip joint and the rotatable artificial knee joint.

2. The method according to claim 1, wherein the step of calculating a current leg angle ($\alpha$) further comprises an equation $$\alpha = \phi_h - \frac{\phi_k}{2}.$$

3. The method according to claim 1, wherein the step of calculating the adjustable leg length (l) further comprises an equation $$l = (l_s + l_t)\sin\frac{\phi_k}{2}.$$

4. The method according to claim 1, wherein the step of applying a first torque or no torque to the rotatable artificial knee joint and/or a first torque to the rotatable artificial hip joint until the adjustable leg length (l) is equal to or less than the leg clearance length ($l_{clr}$) further comprises repeating steps a-c.

5. The method according to claim 1, wherein the step of applying a second torque or no torque to the rotatable artificial knee joint and/or a second torque to the rotatable artificial hip joint until a threshold leg angle $\alpha_{thr}$, defined as ($\alpha_{tgt}+\Delta\alpha_{thr}$), is reached further comprises repeating steps a-c.

6. The method according to claim 1, wherein the step of applying a first torque or no torque to the rotatable artificial knee joint and/or a first torque to the rotatable artificial hip joint until the adjustable leg length (l) is equal to or less than the leg clearance length ($l_{clr}$) further comprises calculating the first torque to the rotatable artificial hip joint based on equation $$\tau_h^\alpha = k_p^\alpha(\alpha_{tgt}-\alpha) - k_d^\alpha\dot{\alpha}.$$

7. The method according to claim 1, wherein the step of applying a second torque or no torque to the rotatable artificial knee joint and/or a second torque to the rotatable artificial hip joint until a threshold leg angle $\alpha_{thr}$, defined as ($\alpha_{tgt}+\Delta\alpha_{thr}$), is reached further comprises calculating the second torque to the rotatable artificial hip joint based on equation $$\tau_h^\alpha = k_p^\alpha(\alpha_{tgt}-\alpha) - k_d^\alpha\dot{\alpha}.$$

8. The method according to claim 7, wherein the step of applying a second torque or no torque to the rotatable artificial knee joint and/or a second torque to the rotatable artificial hip joint until a threshold leg angle $\alpha_{thr}$, defined as ($\alpha_{tgt}+\Delta\alpha_{thr}$), is reached further comprises calculating the second torque to the rotatable artificial hip joint based on equation $T_h = \tau_h^\alpha + \tau_h^{iii}$, wherein $\tau_h^{iii}$ is a compensation torque applied at the rotatable artificial hip joint.

9. The method according to claim 1, wherein the step of applying a first torque or no torque to the rotatable artificial knee joint and/or a first torque to the rotatable artificial hip joint until the adjustable leg length (l) is equal to or less than the leg clearance length ($l_{clr}$) further comprises calculating the first torque or no torque to the rotatable artificial knee joint based on equations $$\tau_k^i = \begin{cases} k^i\dot{\alpha}, & \dot{\alpha} \leq 0 \\ 0, & \dot{\alpha} > 0 \end{cases}.$$

10. The method according to claim 1, wherein the step of applying a second torque or no torque to the rotatable artificial knee joint and/or a second torque to the rotatable artificial hip joint until a threshold leg angle $\alpha_{thr}$, defined as $(\alpha_{tgt}+\Delta\alpha_{thr})$, is reached further comprises calculating the second torque or no torque to the rotatable artificial knee joint based on equations $$\tau_k^{ii} = \begin{cases} -k^{ii}\dot{\phi}_k, & \dot{\phi}_k \leq 0 \\ -k^{ii}\dot{\phi}_k(\alpha - \alpha_{tgt})(\dot{\phi}_k + \dot{\alpha}), & \dot{\phi}_k > 0 \text{ \& } \dot{\phi}_k > -\dot{\alpha} \\ 0, & \text{otherwise} \end{cases}.$$

11. The method according to claim 1, wherein the step of applying a second torque or no torque to the rotatable artificial knee joint and/or a second torque to the rotatable artificial hip joint until a threshold leg angle $\alpha_{thr}$, defined as $(\alpha_{tgt}+\Delta\alpha_{thr})$, is reached further comprises calculating the second torque or no torque to the rotatable artificial knee joint based on equation $$\tau_k^i = \begin{cases} k^i\dot{\alpha}, & \dot{\alpha} \leq 0 \\ 0, & \dot{\alpha} > 0 \end{cases}.$$

12. The method according to claim 1, wherein the step of applying a third torque or no torque to the rotatable artificial knee joint and/or a third torque or no torque to the rotatable artificial hip joint until the current leg angle velocity ($\dot{\alpha}$) equals zero further comprises calculating the third torque or no torque to the rotatable artificial knee joint based on equation $$\tau_k^{iii} = \begin{cases} -k^{stp}(\alpha_{thr} - \alpha)\left(1 - \dfrac{\dot{\alpha}}{\dot{\alpha}_{max}}\right), & \dot{\alpha} < \dot{\alpha}_{thr} \\ & \dot{\alpha} < \dot{\alpha}_{max} \\ 0, & \text{otherwise} \end{cases}.$$

13. The method according to claim 12, wherein the step of applying a third torque or no torque to the rotatable artificial knee joint and/or a third torque or no torque to the rotatable artificial hip joint until the current leg angle velocity ($\dot{\alpha}$) equals zero further comprises calculating the positive torque or the negative torque to the rotatable artificial hip joint based on equation $$\tau_h^{iii} = 2\tau_k^{iii}$$

14. The method according to claim 1, wherein the step of applying a fourth torque or no torque to the rotatable artificial knee joint and/or a fourth torque or no torque to the rotatable artificial hip joint until the artificial foot contacts the target point further comprises calculating the fourth torque to the rotatable artificial knee joint based on equation $$\tau_k^{iii'} = \tau_k^{iii} + k^{ext}(l_0 - l)$$

when the current leg angle velocity ($\dot{\alpha}$) equals zero, where $l_0 = l_t + l_s$, wherein $\tau_k^{iii}$ is a stopping torque applied at the rotatable artificial knee joint.

15. The method according to claim 14, wherein the step of applying a fourth torque or no torque to the rotatable artificial knee joint and/or a fourth torque or no torque to the rotatable artificial hip joint until the artificial foot contacts the target point further comprises calculating the fourth torque to the rotatable artificial hip joint based on equation $$\tau_h^{iii} = -2\tau_k^{iii}.$$

16. A method for placing an artificial foot connected to a prosthetic or robotic limb on to a target point, wherein the method comprises:
providing the prosthetic or robotic limb with an artificial shank having length ($l_s$) coupled to a rotatable artificial knee joint, wherein the rotatable artificial knee joint is coupled to a natural thigh having length ($l_t$) coupled to a rotatable natural hip joint;
providing a knee torque actuator coupled to the rotatable artificial knee joint;
providing a controller in communication with: i. a rotatable natural hip joint sensor to measure a current hip rotation angle ($\phi_h$), ii. a rotatable artificial knee joint sensor to measure a current knee rotation angle ($\phi_k$), and iii. the knee torque actuator to apply a positive or a negative torque to the rotatable artificial knee joint;
inputting into the controller one or more parameters from the group consisting of a target leg angle ($\alpha_t$), a leg clearance length ($l_{clr}$) a stopping gain ($k^{stp}$), an extension gain ($k^{ext}$), a flexing gain ($k_i$), a damping gain ($k^{ii}$), a maximum return leg angle velocity ($\dot{\alpha}_{max}$), and a leg angle threshold delta ($\Delta\alpha_{thr}$);
wherein the controller executes the following steps of the method:
a. continuously measuring the current hip rotation angle ($\phi_h$) and the current knee rotation angle ($\phi_k$);
b. continuously determining a current leg angle velocity ($\dot{\alpha}$) and a current leg angle ($\alpha$) based on the current hip rotation angle ($\phi_h$) and the current knee rotation angle ($\phi_k$);
c. calculating the adjustable leg length (l) based on the current knee rotation angle ($100_k$), the thigh length ($l_t$), and the shank length ($l_s$);
d. applying a first torque or no torque to the rotatable artificial knee joint until the adjustable leg length (l) is equal to or less than the leg clearance length ($l_{clr}$);
e. applying a second torque or no torque to the rotatable artificial knee joint until a threshold leg angle $\alpha_{thr}$, defined as ($\alpha_{tgt}+\Delta\alpha_{thr}$), is reached;
f. applying a third torque or no torque to the rotatable artificial knee joint until the current leg angle velocity ($\dot{\alpha}$) equal to or greater than zero; and
g. applying a fourth torque or no torque to the rotatable artificial knee joint until the artificial foot contacts the target point,
whereby motion of the rotatable artificial knee joint is determined without enforcing reference trajectories of the rotatable natural hip joint and the rotatable artificial knee joint.

17. The method according to claim 16, wherein the step of calculating a current leg angle ($\alpha$) further comprises an equation $$\alpha = \phi_h - \dfrac{\phi_k}{2}.$$

18. The method according to claim 16, wherein the step of calculating the adjustable leg length (l) further comprises an equation $$l = (l_s + l_t)\sin\frac{\phi_k}{2}.$$

19. The method according to claim 16, wherein the step of applying a first torque or no torque to the rotatable artificial knee joint until the adjustable leg length (l) is equal to or less than the leg clearance length ($l_{clr}$) further comprises repeating steps a-c.

20. The method according to claim 16, wherein the step of applying a second torque or no torque to the rotatable artificial knee joint until a threshold leg angle $\alpha_{thr}$, defined as ($\alpha_{tgt}+\Delta\alpha_{thr}$), is reached further comprises repeating steps a-c.

21. The method according to claim 16, wherein the step of applying a first torque or no torque to the rotatable artificial knee joint until the adjustable leg length (l) is equal to or less than the leg clearance length ($l_{clr}$) further comprises calculating the first torque or no torque to the rotatable artificial knee joint based on equations $$\tau_k^i = \begin{cases} k^i\dot\alpha, & \dot\alpha \le 0 \\ 0, & \dot\alpha > 0 \end{cases}.$$

22. The method according to claim 16, wherein the step of applying a second torque or no torque to the rotatable artificial knee joint until a threshold leg angle $\alpha_{thr}$, defined as ($\alpha_{tgt}+\Delta\alpha_{thr}$), is reached further comprises calculating the second torque or no torque to the rotatable artificial knee joint based on equations $$\tau_k^{ii} = \begin{cases} -k^{ii}\dot\phi_k, & \dot\phi_k \le 0 \\ -k^{ii}\dot\phi_k(\alpha-\alpha_{tgt})(\dot\phi_k+\dot\alpha), & \dot\phi_k > 0 \ \& \ \dot\phi_k > -\dot\alpha \\ 0, & \text{otherwise} \end{cases}.$$

23. The method according to claim 16, wherein the step of applying a second torque or no torque to the rotatable artificial knee joint until a threshold leg angle $\alpha_{thr}$, defined as ($\alpha_{tgt}+\Delta\alpha_{thr}$), is reached further comprises calculating the second torque or no torque to the rotatable artificial knee joint based on equation $$\tau_k^i = \begin{cases} k^i\dot\alpha, & \dot\alpha \le 0 \\ 0, & \dot\alpha > 0 \end{cases}.$$

24. The method according to claim 16, wherein the step of applying a third torque or no torque to the rotatable artificial knee joint until the current leg angle velocity ($\dot\alpha$) equals zero further comprises calculating the third torque or no torque to the rotatable artificial knee joint based on equation $$\tau_k^{iii} = \begin{cases} -k^{stp}(\alpha_{thr}-\alpha)\left(1-\dfrac{\dot\alpha}{\dot\alpha_{max}}\right), & \alpha < \alpha_{thr} \\ & \dot\alpha < \dot\alpha_{max} \\ 0, & \text{otherwise} \end{cases}.$$

25. The method according to claim 16, wherein the step of applying a fourth torque or no torque to the rotatable artificial knee joint until the foot contacts the target point further comprises calculating the fourth torque to the rotatable artificial knee joint based on equation $$\tau_k^{iii'} = \tau_k^{iii} + k^{ext}(l_0-l)$$

when the current leg angle velocity ($\dot\alpha$) equals zero, where $l_0=l_t+l_s$, wherein $\tau_k^{iii'}$ is a stopping torque applied at the rotatable artificial knee joint.

* * * * *